(12) United States Patent
Parihar et al.

(10) Patent No.: US 11,602,394 B2
(45) Date of Patent: Mar. 14, 2023

(54) ELECTROSURGICAL DEVICE WITH DISPOSABLE SHAFT HAVING MODULAR SUBASSEMBLY

(71) Applicant: Ethicon LLC, Guaynabo, PR (US)

(72) Inventors: Shailendra K. Parihar, Mason, OH (US); David T. Martin, Milford, OH (US); Gregory W. Johnson, Milford, OH (US); William J. White, West Chester, OH (US)

(73) Assignee: Cilag GmbH International, Zug (CH)

( * ) Notice: Subject to any disclaimer, the term of this patent is extended or adjusted under 35 U.S.C. 154(b) by 245 days.

(21) Appl. No.: 16/712,080

(22) Filed: Dec. 12, 2019

(65) Prior Publication Data

US 2020/0197080 A1 Jun. 25, 2020

Related U.S. Application Data

(60) Continuation of application No. 15/632,868, filed on Jun. 26, 2017, now Pat. No. 10,524,856, which is a
(Continued)

(51) Int. Cl.
*A61B 17/28* (2006.01)
*A61B 18/14* (2006.01)
*A61B 18/18* (2006.01)
*A61B 34/00* (2016.01)
*A61B 34/30* (2016.01)
(Continued)

(52) U.S. Cl.
CPC ...... *A61B 18/1482* (2013.01); *A61B 18/1445* (2013.01); *A61B 18/18* (2013.01); *A61B 34/30* (2016.02); *A61B 34/70* (2016.02); *A61B 2017/0046* (2013.01);
(Continued)

(58) Field of Classification Search
CPC ........ A61B 19/2203; A61B 2017/2943; A61B 17/28; A61B 17/2812; A61B 34/70; A61B 34/71; A61B 2034/07; A61B 2034/15
See application file for complete search history.

(56) References Cited

U.S. PATENT DOCUMENTS 5,792,135 A   8/1998   Madhani et al.
5,817,084 A   10/1998  Jensen
(Continued)

OTHER PUBLICATIONS

International Search Report and Written Opinion dated Sep. 15, 2014 for International Application No. PCT/US2014/016422, 13 pages.
(Continued)

*Primary Examiner* — Allen Porter
(74) *Attorney, Agent, or Firm* — Frost Brown Todd LLP

(57) ABSTRACT

An apparatus comprises an end effector, a shaft assembly, and an interface assembly. The end effector is operable to manipulate tissue, the shaft assembly is in communication with the end effector and a portion of the shaft assembly extends proximally from the end effector. The interface assembly is in communication with the shaft assembly. The interface assembly comprises a housing portion, a shaft cartridge, and a base portion. The housing portion can engage the shaft cartridge. The shaft cartridge is able to rotate and articulate the end effector, and the shaft assembly extends from the shaft cartridge. The base portion and the housing portion are able to enclose the shaft cartridge.

18 Claims, 27 Drawing Sheets

Related U.S. Application Data continuation of application No. 14/993,268, filed on Jan. 12, 2016, now Pat. No. 9,707,033, which is a division of application No. 13/798,712, filed on Mar. 13, 2013, now Pat. No. 9,254,170.

(51) Int. Cl.
  *A61B 17/29* (2006.01)
  *A61B 17/00* (2006.01)

(52) U.S. Cl.
  CPC ............ *A61B 2017/00477* (2013.01); *A61B 2017/2943* (2013.01); *A61B 2018/1455* (2013.01)

(56) References Cited

U.S. PATENT DOCUMENTS

| | | | |
|---|---|---|---|
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,500,176 B1 | 12/2002 | Truckai et al. | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckal et al. | |
| 7,380,696 B2 | 6/2008 | Shelton, IV et al. | |
| 7,381,209 B2 | 6/2008 | Truckai et al. | |
| 7,404,508 B2 | 7/2008 | Smith et al. | |
| 7,455,208 B2 | 11/2008 | Wales et al. | |
| 7,506,790 B2 | 3/2009 | Shelton, IV et al. | |
| 7,524,320 B2 | 4/2009 | Tierney et al. | |
| 7,549,564 B2 | 6/2009 | Boudreaux | |
| 7,559,450 B2 | 7/2009 | Wales et al. | |
| 7,654,431 B2 | 2/2010 | Hueil et al. | |
| 7,691,098 B2 | 4/2010 | Wallace et al. | |
| 7,780,054 B2 | 8/2010 | Wales | |
| 7,784,662 B2 | 8/2010 | Wales et al. | |
| 7,798,386 B2 | 9/2010 | Schall et al. | |
| 7,806,891 B2 | 10/2010 | Nowlin et al. | |
| 7,824,401 B2 | 11/2010 | Manzo et al. | |
| 8,317,745 B2 | 11/2012 | Kirschenman et al. | |
| 8,461,744 B2 | 6/2013 | Wiener et al. | |
| 8,479,969 B2 | 7/2013 | Shelton, IV et al. | |
| 8,485,413 B2 | 7/2013 | Scheib et al. | |
| 8,573,461 B2 | 11/2013 | Shelton, IV et al. | |
| 8,573,465 B2 | 11/2013 | Shelton, IV | |
| 8,602,031 B2 | 12/2013 | Reis et al. | |
| 8,602,288 B2 | 12/2013 | Shelton, IV et al. | |
| 8,616,431 B2 | 12/2013 | Timm et al. | |
| 8,752,749 B2 | 6/2014 | Moore et al. | |
| 8,783,541 B2 | 7/2014 | Shelton, IV et al. | |
| 8,800,838 B2 | 8/2014 | Shelton, IV et al. | |
| 8,820,605 B2 | 9/2014 | Shelton, IV et al. | |
| 8,844,789 B2 | 9/2014 | Shelton, IV et al. | |
| 8,939,974 B2 | 1/2015 | Boudreaux et al. | |
| 8,951,248 B2 | 2/2015 | Messerly et al. | |
| 8,956,349 B2 | 2/2015 | Aldridge et al. | |
| 8,986,302 B2 | 3/2015 | Aldridge et al. | |
| 9,023,071 B2 | 5/2015 | Miller et al. | |
| 9,039,695 B2 | 5/2015 | Giordano et al. | |
| 9,050,093 B2 | 6/2015 | Aldridge et al. | |
| 9,060,776 B2 | 6/2015 | Yates et al. | |
| 9,089,327 B2 | 7/2015 | Worrell et al. | |
| 9,089,360 B2 | 7/2015 | Messerly et al. | |
| 9,095,362 B2 | 8/2015 | Dachs et al. | |
| 9,161,803 B2 | 10/2015 | Yates et al. | |
| 9,220,559 B2 | 12/2015 | Worrell et al. | |
| 9,254,170 B2 | 2/2016 | Parihar et al. | |
| 9,301,759 B2 | 4/2016 | Spivey et al. | |
| 9,402,682 B2 | 8/2016 | Worrell et al. | |
| 9,545,253 B2 | 1/2017 | Worrell et al. | |
| 9,707,033 B2 | 7/2017 | Parihar et al. | |
| 9,814,457 B2 | 11/2017 | Martin et al. | |
| 9,877,720 B2 | 1/2018 | Worrell et al. | |
| 10,524,856 B2 | 1/2020 | Parihar et al. | |
| 2002/0143319 A1* | 10/2002 | Brock | A61B 5/0086 606/1 |
| 2002/0188293 A1* | 12/2002 | Manzo | A61B 34/30 606/45 |
| 2006/0079874 A1 | 4/2006 | Faller et al. | |
| 2007/0191713 A1 | 8/2007 | Eichmann et al. | |
| 2007/0221700 A1* | 9/2007 | Ortiz | A61B 17/1633 227/175.1 |
| 2007/0282333 A1 | 12/2007 | Fortson et al. | |
| 2008/0200940 A1 | 8/2008 | Eichmann et al. | |
| 2010/0010505 A1 | 1/2010 | Herlihy et al. | |
| 2011/0118708 A1 | 5/2011 | Burbank et al. | |
| 2011/0290855 A1* | 12/2011 | Moore | A61B 17/07207 227/180.1 |
| 2012/0078248 A1 | 3/2012 | Worrell et al. | |
| 2012/0150192 A1* | 6/2012 | Dachs, II | A61B 34/70 606/130 |
| 2014/0249472 A1* | 9/2014 | Mulvihill | A61M 1/83 604/95.01 |

OTHER PUBLICATIONS

U.S. Appl. No. 61/550,768, filed Oct. 24, 2011.
U.S. Appl. No. 61/597,603, filed Feb. 10, 2012.

\* cited by examiner

ELECTROSURGICAL DEVICE WITH DISPOSABLE SHAFT HAVING MODULAR SUBASSEMBLY

This application is a continuation of U.S. patent application Ser. No. 15/632,868, entitled "Electrosurgical Device with Disposable Shaft Having Modular Subassembly," filed Jun. 26, 2017 and issued as U.S. Pat. No. 10,524,856 on Jan. 7, 2020, which is a continuation of U.S. patent application Ser. No. 14/993,268, entitled "Electrosurgical Device with Disposable Shaft Having Modular Subassembly," filed Jan. 12, 2016 and issued as U.S. Pat. No. 9,707,033 on Jul. 18, 2017, which is a divisional of U.S. patent application Ser. No. 13/798,712, entitled "Electrosurgical Device with Disposable Shaft Having Modular Subassembly," filed Mar. 13, 2013 and issued as U.S. Pat. No. 9,254,170 on Feb. 9, 2016.

BACKGROUND

A variety of surgical instruments include a tissue cutting element and one or more elements that transmit radio frequency (RF) energy to tissue (e.g., to coagulate or seal the tissue). An example of an RF electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pub. No. 2012/0078247, entitled "Articulation Joint Features for Articulating Surgical Device," published Mar. 29, 2012, issued as U.S. Pat. No. 9,402,682 on Aug. 2, 2016, the disclosure of which is incorporated by reference herein; U.S. Pub. No. 2013/0030428, entitled "Surgical Instrument with Multi-Phase Trigger Bias," published Jan. 31, 2013, issued as U.S. Pat. No. 9,089,327 on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, issued as U.S. Pat. No. 9,545,253 on Jan. 17, 2017, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

Some surgical systems provide robotic control of a surgical instrument. With minimally invasive robotic surgery, surgical operations may be performed through a small incision in the patient's body. A robotic surgical system may be used with various types of surgical instruments, including but not limited to surgical staplers, ultrasonic instruments, electrosurgical instruments, and/or various other kinds of instruments, as will be described in greater detail below. An example of a robotic surgical system is the DAVINCI™ system by Intuitive Surgical, Inc., of Sunnyvale, Calif. By way of further example, one or more aspects of robotic surgical systems are disclosed in the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive." issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and U.S. Pat. No. 7,824,401, entitled "Surgical Tool With Writed Monopolar Electrosurgical End Effectors," issued Nov. 2, 2010, the disclosure of which is incorporated by reference herein.

Additional examples of instruments that may be incorporated with a robotic surgical system are described in U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/ 0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/ 0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/ 0203247, entitled "Robotically-Controlled Surgical End Effector System," published Aug. 9, 2012, issued as U.S. Pat. No. 8,783,451 on Jul. 22, 2014, the disclosure of which is incorporated by reference herein; U.S. Pub. No. 2012/ 0211546, entitled "Drive Interface for Operably Coupling a Manipulatable Surgical Tool to a Robot," published Aug. 23, 2012, issued as U.S. Pat. No. 8,479,969 on Jul. 9, 2013, the disclosure of which is incorporated by reference herein; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein; U.S. patent application Ser. No. 13/443,101, entitled "Control Interface for Laparoscopic Suturing Instrument," filed Apr. 10, 2012, issued as U.S. Pat. No. 9,814,457 on Nov. 14, 2017, the disclosure of which is incorporated by reference herein; and U.S. Provisional Pat. App. No. 61/597,603, entitled "Robotically Controlled Surgical Instrument," filed Feb. 10, 2012, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
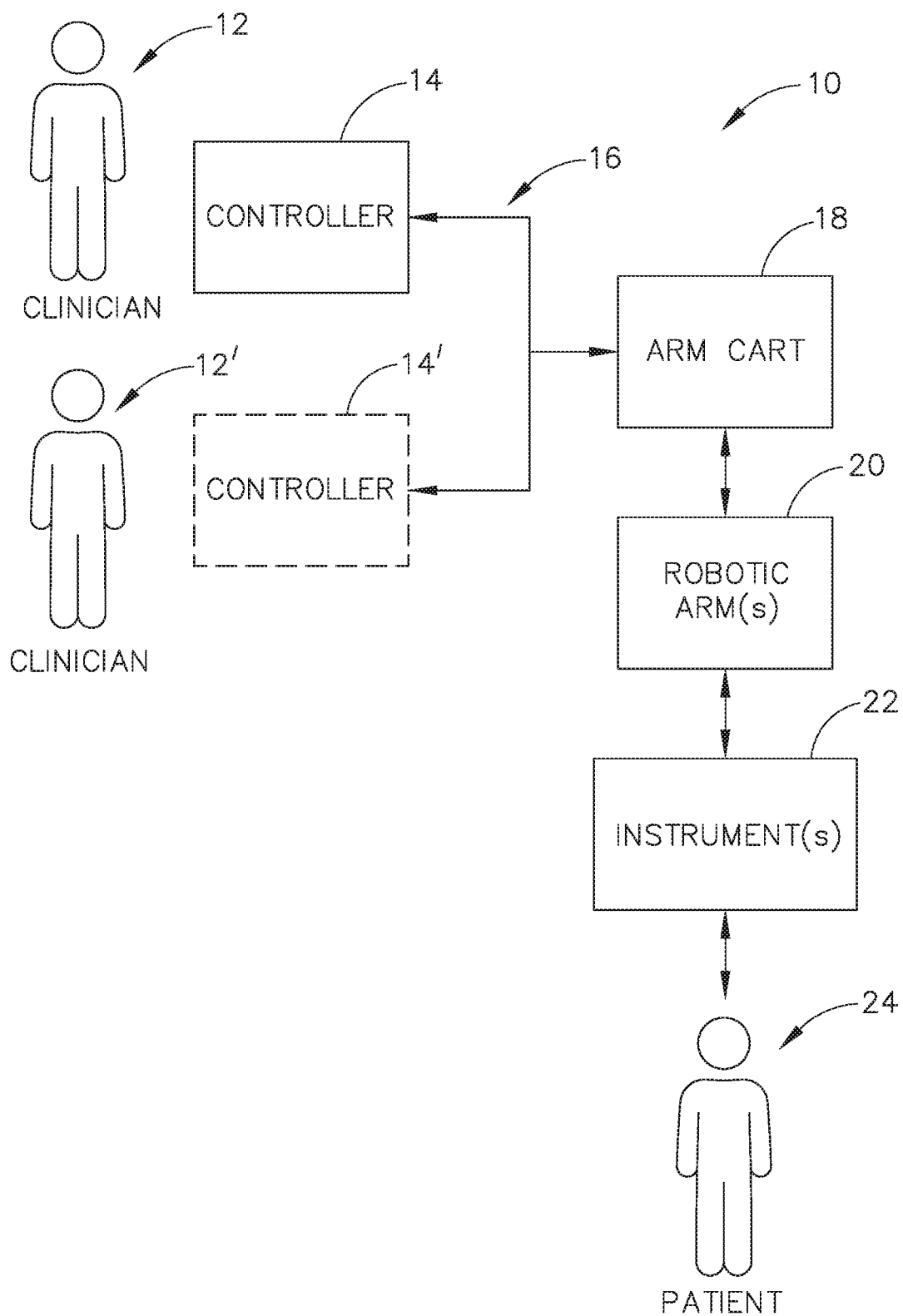
FIG. 1 depicts a block diagram of an exemplary robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a robotic surgical driver comprising a proximal housing having an interface that mechanically and electrically couples with a surgical instrument having a distal surgical end effector. The term "proximal" refers the position of an element closer to the robotic surgical driver housing and the term "distal" refers to the position of an element closer to the surgical end effector of the surgical instrument and further away from the housing.

I. Exemplary Robotic Surgical System Overview

FIG. 1 illustrates an exemplary robotic surgical system (10). System (10) comprises at least one controller (14) and at least one arm cart (18). Arm cart (18) is mechanically and/or electrically coupled to one or more robotic manipulators or arms (20). Each robotic arm (20) comprises one or more surgical instruments (22) for performing various surgical tasks on a patient (24). Operation of arm cart (18), including arms (20) and instruments (22), may be directed by a clinician (12) from controller (14). In some examples, a second controller (14'), operated by a second clinician (12'), may also direct operation of the arm cart (18) in conjunction with the first clinician (12'). For example, each of the clinicians (12, 12') may control different arms (20) of the cart or, in some cases, complete control of arm cart (18) may be passed between the clinicians (12, 12'). In some examples, additional arm carts (not shown) may be utilized on the patient (24). These additional arm carts may be controlled by one or more of the controllers (14, 14').

Arm cart(s) (18) and controllers (14, 14') may be in communication with one another via a communications link (16), which may be any suitable type of wired and/or wireless communications link carrying any suitable type of signal (e.g., electrical, optical, infrared, etc.) according to any suitable communications protocol. Communications link (16) may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network.

Figure 2:
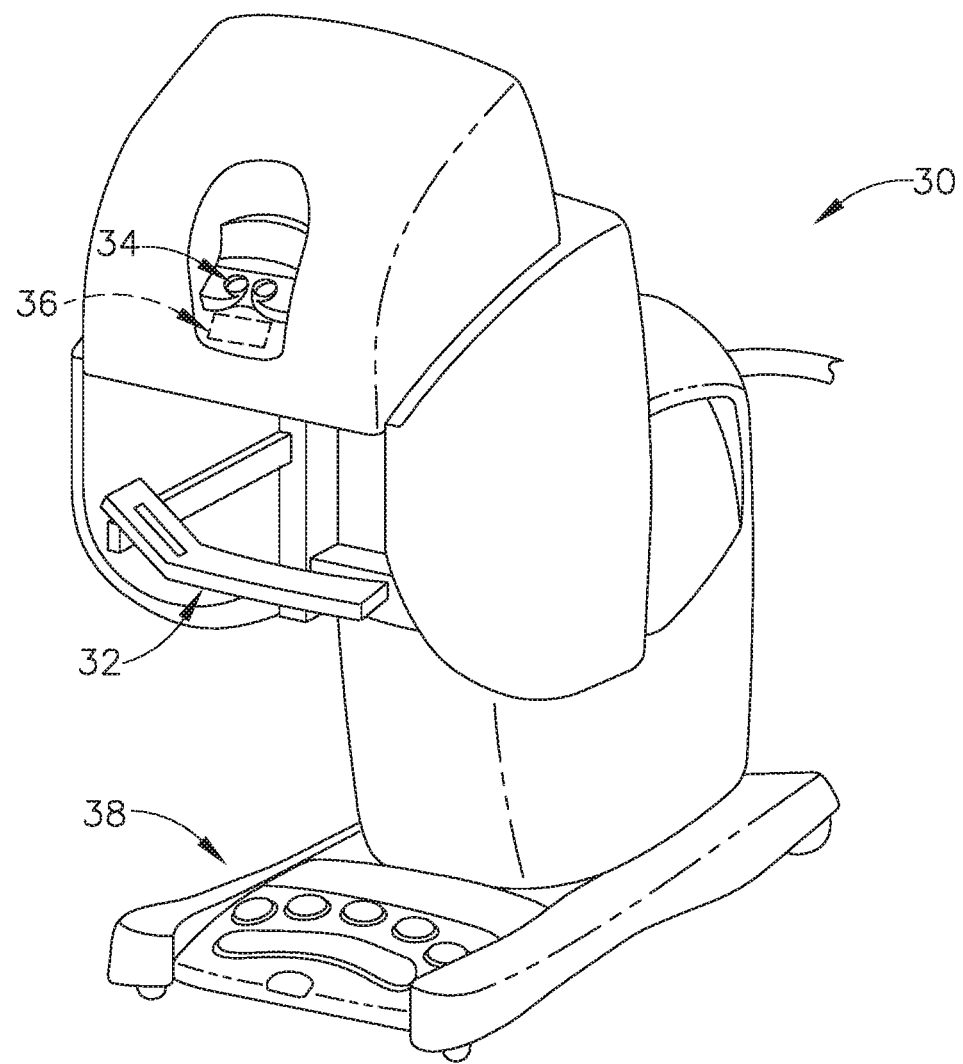
FIG. 2 depicts a perspective view of an exemplary controller of the system of FIG. 1.

FIG. 2 shows an exemplary controller (30) that may serve as a controller (14) of system (10). In this example, controller (30) generally includes user input assembly (32) having precision user input features (not shown) that are grasped by the surgeon and manipulated in space while the surgeon views the surgical procedure via a stereo display (34). The user input features of user input assembly (32) may include manual input devices that move with multiple degrees of freedom; and that include an actuatable handle for intuitively actuating tools (e.g., for closing grasping saws, applying an electrical potential to an electrode, etc). Controller (30) of the present example also includes an array of footswitches (38) providing additional control of arms (20) and instruments (22) to the surgeon. Display (34) may show views from one or more endoscopes viewing the surgical site within the patient and/or any other suitable view(s). In addition, a feedback meter (36) may be viewed through the display (34) and provide the surgeon with a visual indication of the amount of force being applied to a component of instrument (22) (e.g., a cutting member or clamping member, etc.). Other sensor arrangements may be employed to provide controller (30) with an indication as to whether a staple cartridge has been loaded into an end effector of instrument (22), whether an anvil of instrument (22) has been moved to a closed position prior to firing, and/or some other operational condition of instrument (22).

Figure 3:
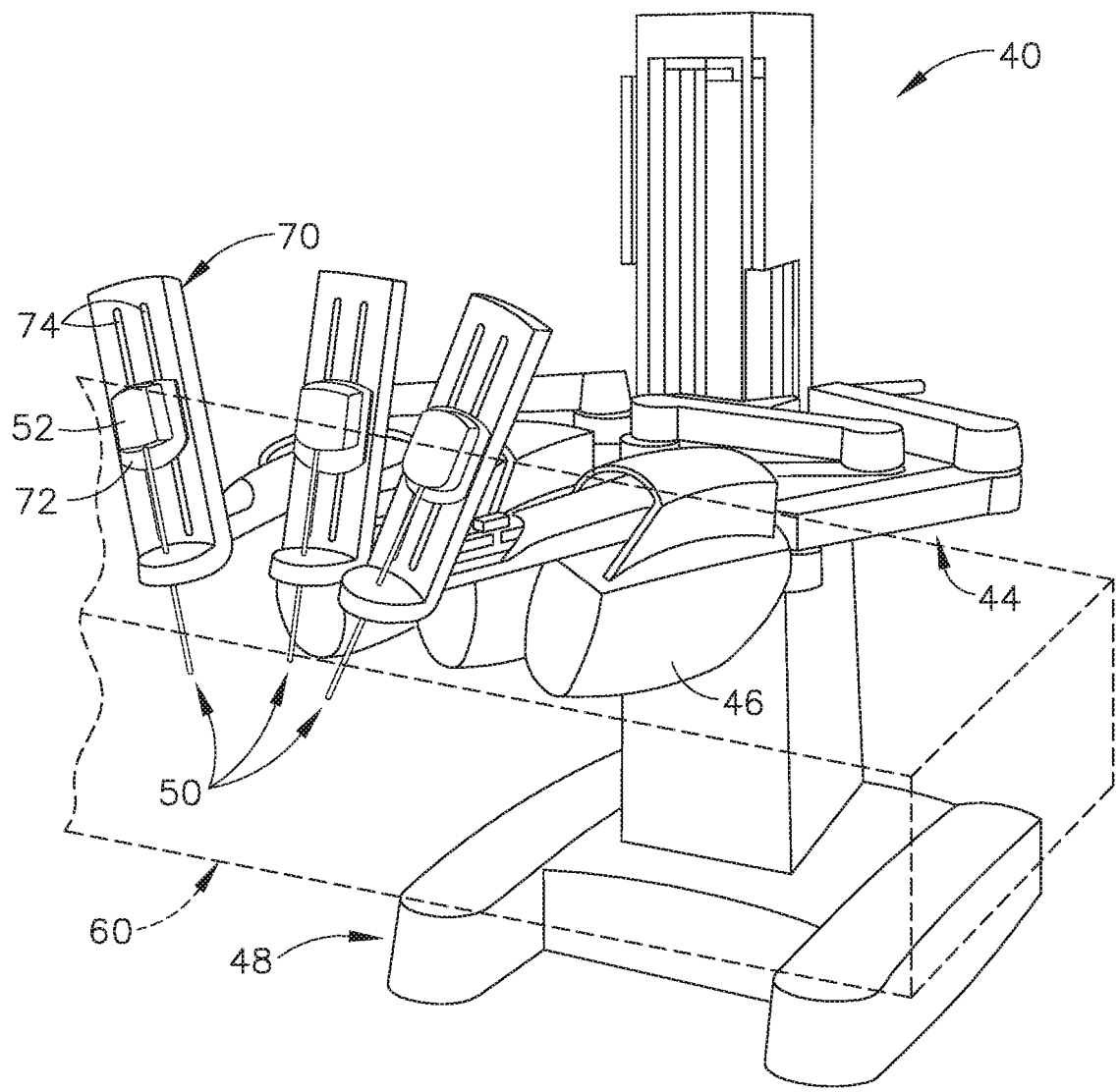
FIG. 3 depicts a perspective view of an exemplary robotic arm cart of the system of FIG. 1.
Figure 4:
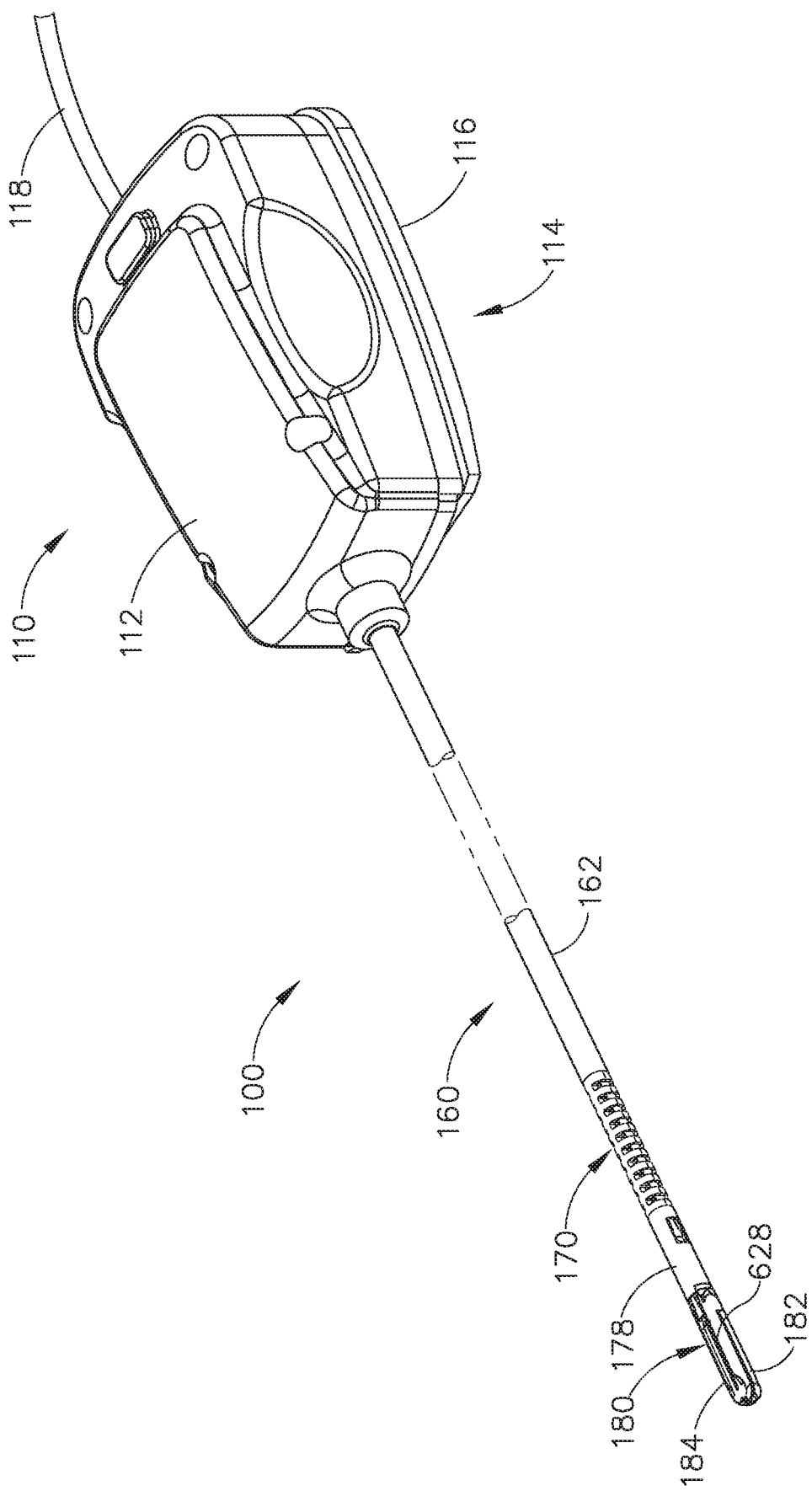
FIG. 4 depicts a perspective view of an exemplary surgical instrument suitable for incorporation with the system of FIG. 1.

FIG. 3 shows an exemplary robotic arm cart (40) that may serve as of arm cart (18) of system (10). In this example, arm cart (40) is operable to actuate a plurality of surgical instruments (50). While three instruments (50) are shown in this example, it should be understood that arm cart (40) may be operable to support and actuate any suitable number of surgical instruments (50). Surgical instruments (50) are each supported by a series of manually articulatable linkages, generally referred to as set-up joints (44), and a robotic manipulator (46). These structures are herein illustrated with protective covers extending over much of the robotic linkage. These protective covers may be optional, and may be limited in size or entirely eliminated in some versions to minimize the inertia that is encountered by the servo mechanisms used to manipulate such devices, to limit the volume of moving components so as to avoid collisions, and to limit the overall weight of cart (40).

Each robotic manipulator (46) terminates at an instrument platform (70), which is pivotable, rotatable, and otherwise movable by manipulator (46). Each platform includes an instrument dock (72) that is slidable along a pair of tracks (74) to further position instrument (50). Such sliding is motorized in the present example. Each instrument dock (72) includes mechanical and electrical interfaces that couple with an interface assembly (52) of instrument (50). By way of example only, dock (72) may include four rotary outputs that couple with complementary rotary inputs of interface assembly (52). Such rotary drive features may drive various functionalities in instrument (50), such as is described in various references cited herein and/or as is described in greater detail below. Electrical interfaces may establish communication via physical contact, inductive coupling, and/or otherwise; and may be operable to provide electrical power to one or more features in instrument (50), provide commands and/or data communication to instrument (50), and/or provide commands and/or data communication from instrument (50). Various suitable ways in which an instrument dock (72) may mechanically and electrically communicate with an interface assembly (52) of an instrument (50) will be apparent to those of ordinary skill in the art in view of the teachings herein. It should also be understood that instrument (50) may include one or more cables that couple with a separate power source and/or control unit, to provide communication of power and/or commands/data to/from instrument (50).

Arm cart (40) of the present example also includes a base (48) that is movable (e.g., by a single attendant) to selectively position arm cart (40) in relation to a patient. Cart (40) may generally have dimensions suitable for transporting the cart (40) between operating rooms. Cart (40) may be configured to fit through standard operating room doors and onto standard hospital elevators. In some versions, an automated instrument reloading system (not shown) may also be positioned in or near the work envelope (60) of arm cart (40), to selectively reload components (e.g., staple cartridges, etc.) of instruments (50).

In addition to the foregoing, it should be understood that one or more aspects of system (10) may be constructed in accordance with at least some of the teachings of U.S. Pat. Nos. 5,792,135; 5,817,084; 5,878,193; 6,231,565; 6,783,524; 6,364,888; 7,524,320; 7,691,098; 7,806,891; 7,824,401; and/or U.S. Pub. No. 2013/0012957, issued as U.S. Pat. No. 8,844,789. The disclosures of each of the foregoing U.S. Patents and U.S. Patent Publication are incorporated by reference herein. Still other suitable features and operabilities that may be incorporated into system (10) will be apparent to those of ordinary skill in the art in view of the teachings herein.

II. Exemplary Electrosurgical Instrument with Articulation Feature

FIGS. 4-13 show an exemplary electrosurgical instrument (100) that may be used as at least one instrument (50) within system (10). At least part of instrument (100) may be constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218, issued as U.S. Pat. No. 8,939,974; U.S. Pub. No. 2012/0116379, issued as U.S. Pat. No. 9,161,803; U.S. Pub. No. 2012/0078243, issued as U.S. Pat. No. 9,877,720; U.S. Pub. No. 2012/0078247, issued as U.S. Pat. No. 9,402,682; U.S. Pub. No. 2013/0030428, issued as U.S. Pat. No. 9,089,327; and/or U.S. Pub. No. 2013/0023868, issued as U.S. Pat. No. 9,545,253. As described therein and as will be described in greater detail below, instrument (100) is operable to cut tissue and seal or weld tissue (e.g., a blood vessel, etc.) substantially simultaneously. In other words, instrument (100) operates similar to an endocutter type of stapler, except that instrument (100) provides tissue welding through application of bipolar RF energy instead of providing lines of staples to join tissue. It should also be understood that instrument (100) may have various structural and functional similarities with the ENSEAL® Tissue Sealing Device by Ethicon Endo-Surgery, Inc., of Cincinnati, Ohio. Furthermore, instrument (100) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to instrument (100), there is no intent for any of the description herein to be presumed as admitted prior art. Several teachings herein will in fact go beyond the scope of the teachings of the references cited herein and the ENSEAL® Tissue Sealing Device by Ethicon Endo-Surgery, Inc., of Cincinnati, Ohio.

Instrument (100) of the present example includes an interface assembly (110), a shaft assembly (160), an articulation section (170), and an end effector (180). Interface assembly (110) is configured to couple with a dock (72) of robotic arm cart (40) and is thereby further operable to drive articulation section (170) and end effector (180) as will be described in greater detail below. As will also be described in greater detail below, instrument (100) is operable to articulate end effector (180) to provide a desired positioning relative to tissue (e.g., a large blood vessel, etc.), then sever the tissue and apply bipolar RF energy to the tissue with end effector (180) to thereby seal the tissue.

A. Exemplary Shaft Assembly and Articulation Section

Figure 5:
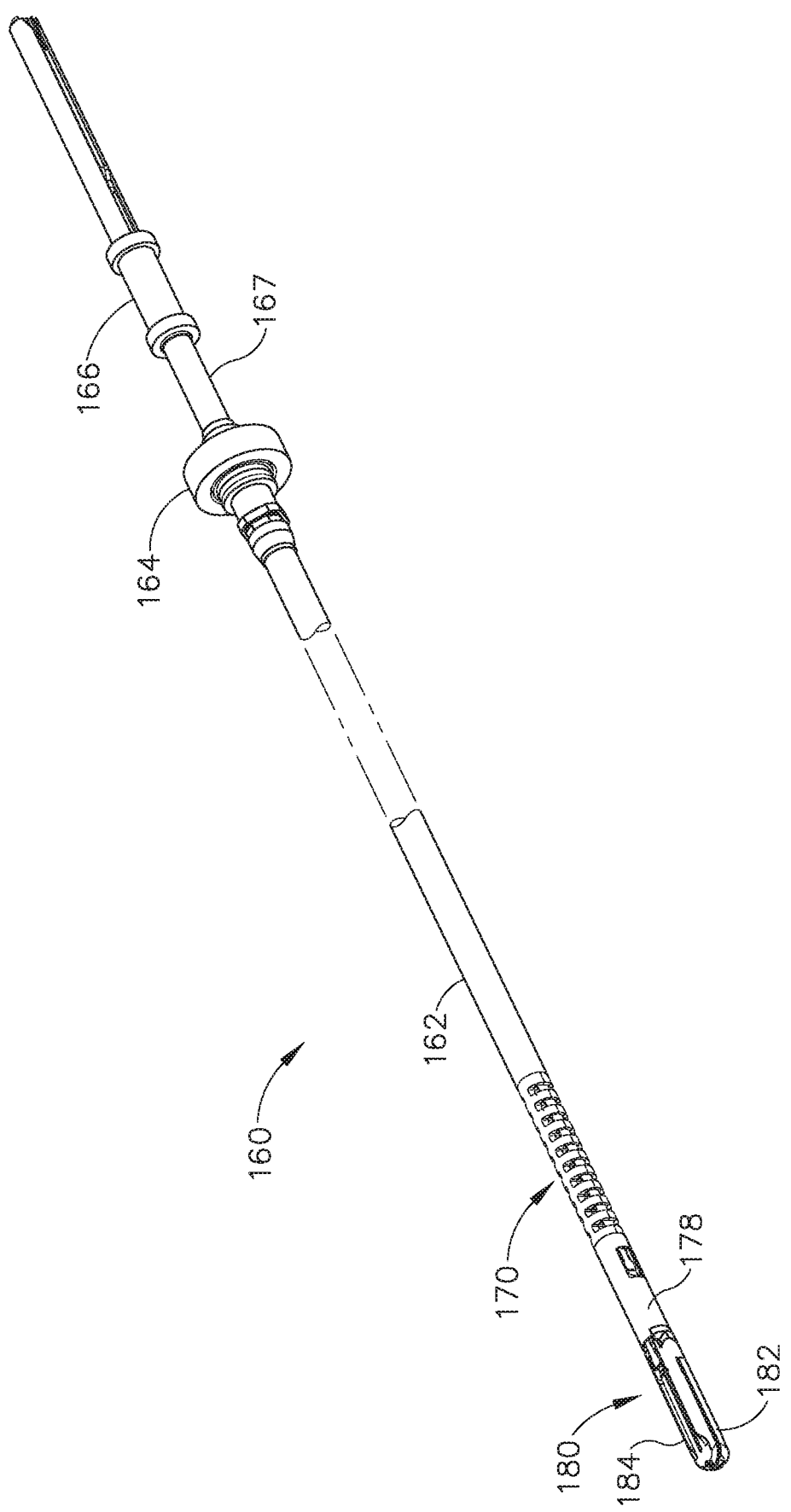
FIG. 5 depicts a perspective view of the shaft assembly of the surgical instrument of FIG. 4.

Shaft assembly (160) of the present example extends distally from interface assembly (110). Articulation section (170) is located at the distal end of shaft assembly (160), with end effector (180) being located distal to articulation section (170). Shaft assembly (160) includes an outer sheath (162) that encloses drive features and electrical features that couple interface assembly (110) with articulation section (170) and end effector (180). As best seen in FIG. 5, shaft assembly (160) further includes a unitary rotary coupling (164) and a firing beam coupling (166). Shaft assembly (160) is rotatable about the longitudinal axis defined by sheath (162), relative to interface assembly (110), via rotary coupling (164). Such rotation may provide rotation of end effector (180), articulation section (170), and shaft assembly (160) unitarily. In some other versions, rotary coupling (164) is operable to rotate end effector (180) without rotating any portion of shaft assembly (160) that is proximal of articulation section (170). As another merely illustrative example, instrument (100) may include one rotation control that provides rotatability of shaft assembly (160) and end effector (180) as a single unit; and another rotation control that provides rotatability of end effector (180) without rotating any portion of shaft assembly (160) that is proximal of articulation section (170). Other suitable rotation schemes will be apparent to those of ordinary skill in the art in view of the teachings herein. Of course, rotatable features may simply be omitted if desired.

Articulation section (170) is operable to selectively position end effector (180) at various angles relative to the longitudinal axis defined by sheath (162). Articulation section (170) may take a variety of forms. By way of example only, articulation section (170) may be configured in accordance with one or more teachings of U.S. Pub. No. 2012/0078247, issued as U.S. Pat. No. 9,402,682, the disclosure of which is incorporated by reference herein. As another merely illustrative example, articulation section (170) may be configured in accordance with one or more teachings of U.S. Pub. No. 2012/0078248, entitled "Articulation Joint Features for Articulating Surgical Device," published Mar. 29, 2012, issued as U.S. Pat. No. 9,220,559 on Dec. 29, 2015, the disclosure of which is incorporated by reference herein. Various other suitable forms that articulation section (170) may take will be apparent to those of ordinary skill in the art in view of the teachings herein. It should also be understood that some versions of instrument (10) may simply lack articulation section (170).

Figure 6:
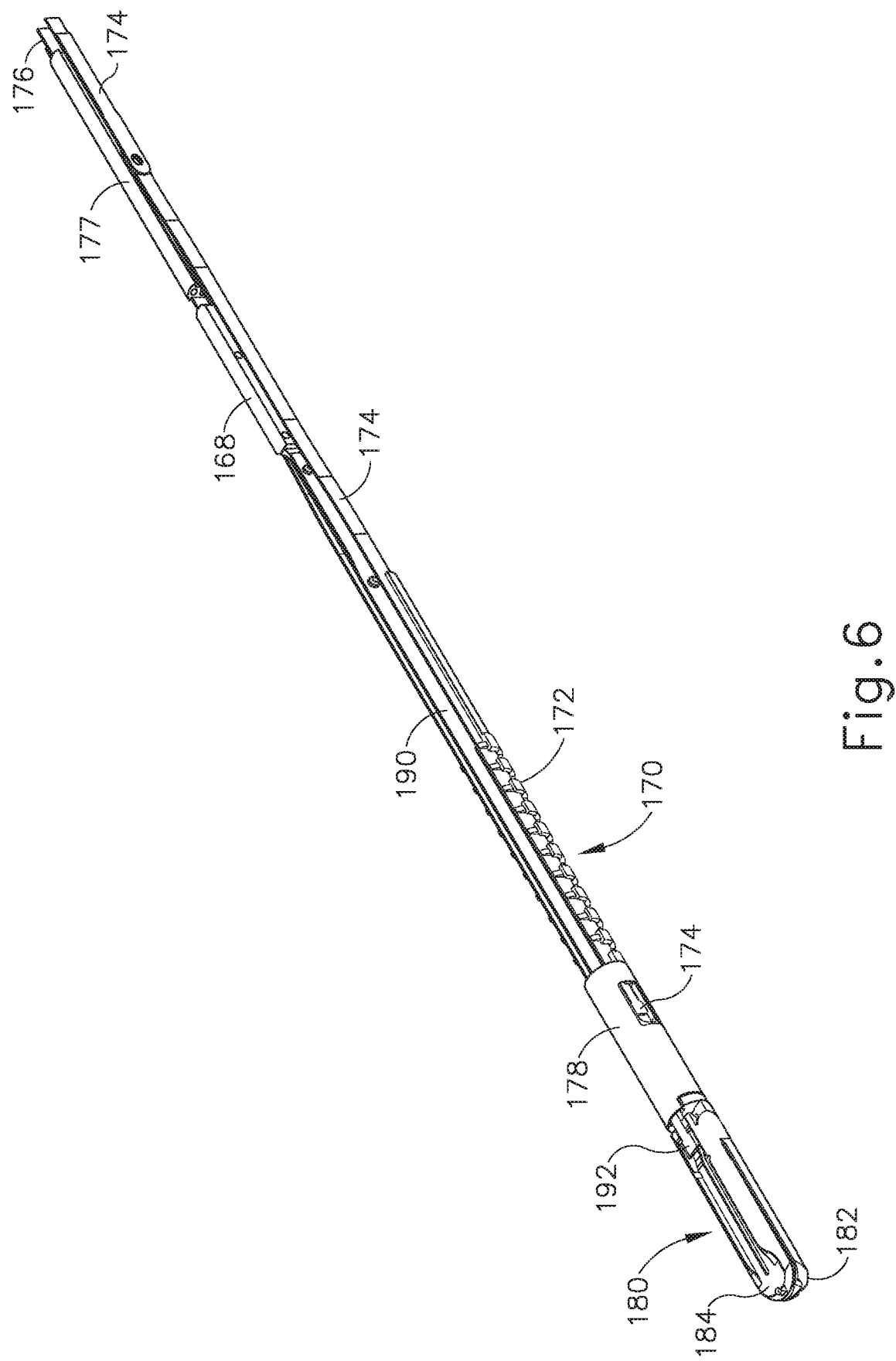
FIG. 6 depicts a perspective view of components of the shaft assembly of FIG. 5.
Figure 7:
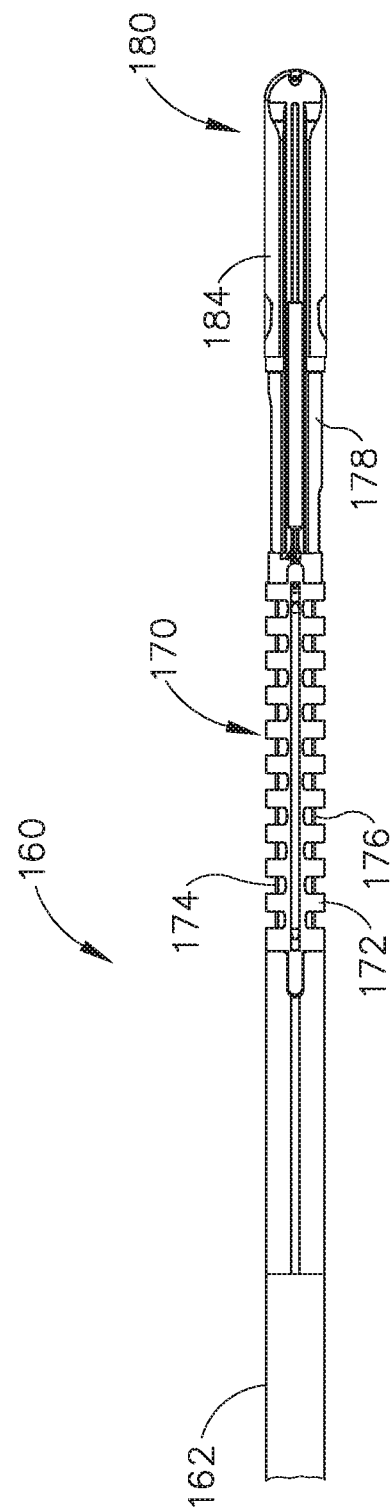
FIG. 7 depicts a top plan view of a distal portion of the shaft assembly of FIG. 5.

As best seen in FIGS. 6-7, articulation section (170) of the present example comprises a ribbed body (172) with a pair of articulation beams (174, 176) extending through ribbed body (172). An upper half of ribbed body (172) is omitted in FIG. 6. Articulation beams (174, 176) are distally anchored within a tube (178) that is positioned between end effector (180) and articulation section (170). Articulation beams (174, 176) are operable to articulate end effector (180) by laterally deflecting end effector (180) away from the longitudinal axis defined by sheath (162). In particular, and referring to the view shown in FIG. 7, end effector (180) will deflect toward articulation beam (174) when articulation beam (174) is retracted proximally while articulation beam (176) is advanced distally. End effector (180) will deflect toward articulation beam (176) when articulation beam (176) is retracted proximally while articulation beam (174) is advanced distally. Merely illustrative examples of how articulation beams (174, 176) may be opposingly translated will be described in greater detail below, while still other examples will be apparent to those of ordinary skill in the art in view of the teachings herein. As best seen in FIG. 6, a spacer body (177) is positioned between articulation beams (174, 176) and is operable to maintain beams (174, 176) in a substantially straight, separated relationship.

B. Exemplary End Effector

End effector (180) of the present example comprises a first jaw (182) and a second jaw (184). In the present example, first jaw (182) is substantially fixed relative to shaft assembly (160); while second jaw (184) pivots relative to shaft assembly (160), toward and away from first jaw (182). In some versions, actuators such as rods or cables, etc., may extend through sheath (162) and be joined with second jaw (184) at a pivotal coupling, such that longitudinal movement of the actuator rods/cables/etc. through shaft assembly (160) provides pivoting of second jaw (184) relative to shaft assembly (160) and relative to first jaw (182). Of course, jaws (182, 184) may instead have any other suitable kind of movement and may be actuated in any other suitable fashion. By way of example only, and as will be described in greater detail below, jaws (182, 184) may be actuated and thus closed by longitudinal translation of a firing beam (190), such that actuator rods/cables/etc. may simply be eliminated in some versions.

Figure 8:
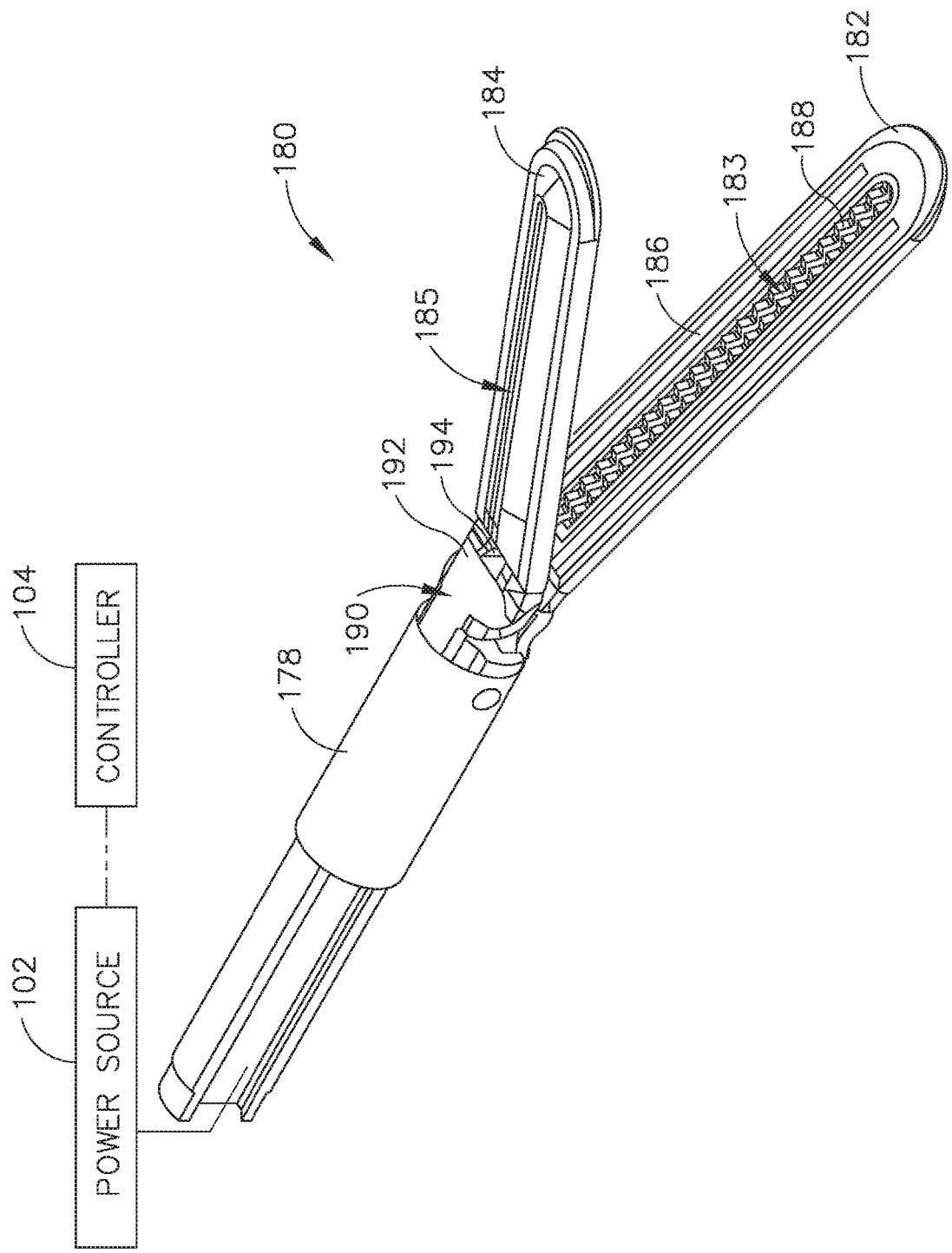
FIG. 8 depicts a perspective view of the end effector of the shaft assembly of FIG. 5, in an open configuration.
Figure 9:
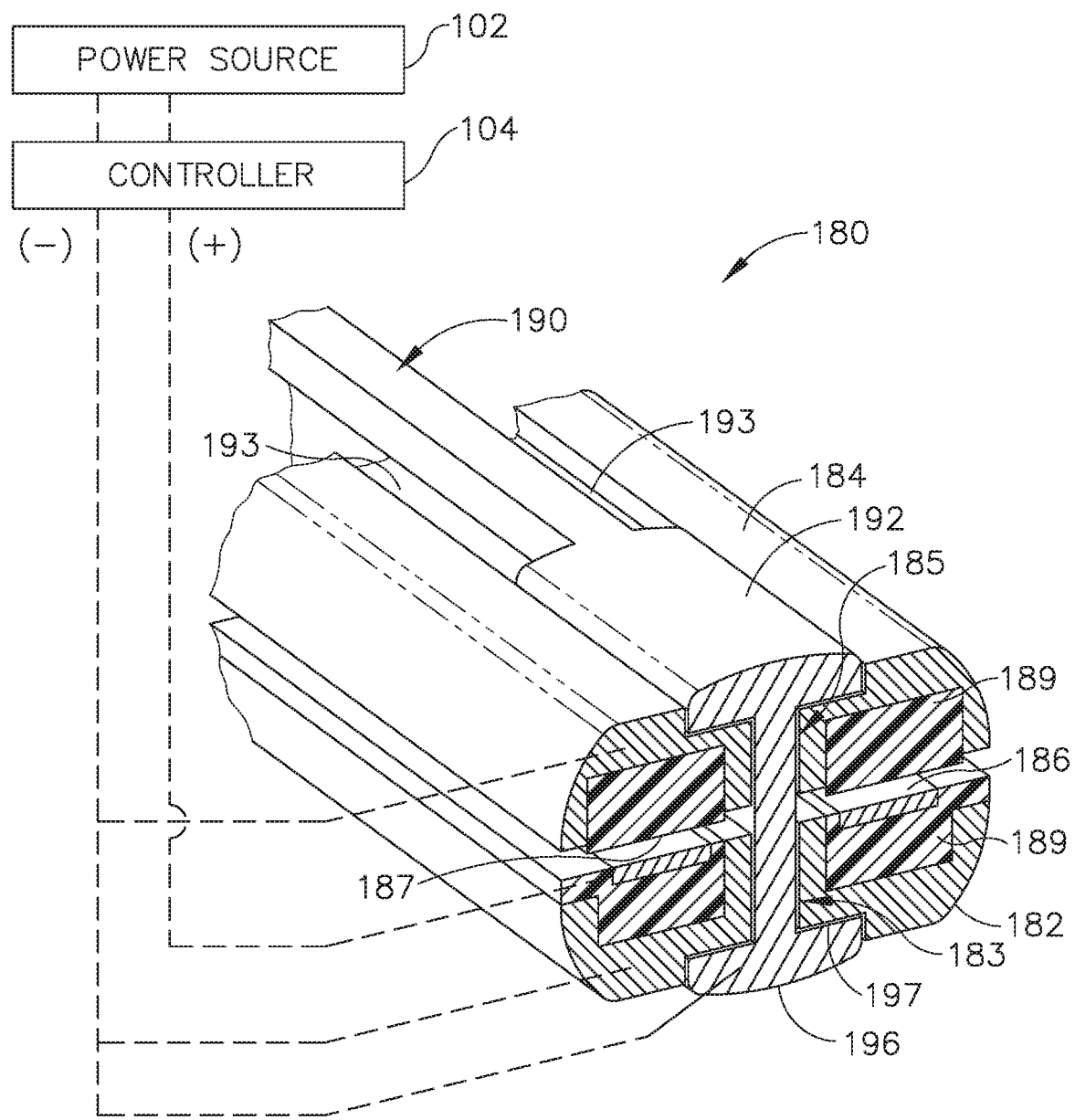
FIG. 9 depicts a perspective view in cross-section of the end effector of FIG. 8, taken along a lateral plane, with the end effector in a closed configuration.

As best seen in FIGS. 8-9, first jaw (182) defines a longitudinally extending elongate slot (183); while second jaw (184) also defines a longitudinally extending elongate slot (185). In addition, the top side of first jaw (182) presents a first electrode surface (186); while the underside of second jaw (184) presents a second electrode surface (187). Electrode surface (186, 187) are in communication with an electrical source (102) via one or more conductors (not shown) that extend along the length of shaft assembly (160). Electrical source (102) is operable to deliver RF energy to first electrode surface (186) at a first polarity and to second electrode surface (187) at a second (opposite) polarity, such that RF current flows between electrode surface (186, 187) and thereby through tissue captured between jaws (182, 184). In some versions, firing beam (190) serves as an electrical conductor that cooperates with electrode surface (186, 187) (e.g., as a ground return) for delivery of bipolar RF energy captured between jaws (182, 184).

Electrical source (102) may be external to instrument (100) or may be integral with instrument (100), as described in one or more references cited herein or otherwise. A controller (104) regulates delivery of power from electrical source (102) to electrode surfaces (186, 187). Controller (104) may also be external to instrument (100) or may be integral with electrosurgical instrument (100), as described in one or more references cited herein or otherwise. It should also be understood that electrode surfaces (186, 187) may be provided in a variety of alternative locations, configurations, and relationships. It should also be understood that power source (102) and/or controller (104) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, issued as U.S. Pat. No. 9,089,360 on Jul. 28, 2015, the disclosure of which is incorporated by reference herein; U.S. Pub. No. 2011/0087212, entitled "Surgical Generator for Ultrasonic and Electrosurgical Devices," published Apr. 14, 2011 issued as U.S. Pat. No. 8,986,302 on Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, issued as U.S. Pat. No. 8,951,248 on Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, issued as U.S. Pat. No. 9,039,695 on May 26, 2015, the disclosure of which is incorporated by reference herein; U.S. Pub. No. 2011/0087215, entitled "Surgical Generator for Ultrasonic and Electrosurgical Devices," published Apr. 14, 2011, issued as U.S. Pat. No. 9,050,093 on Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, issued as U.S. Pat. No. 8,956,349 on Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, issued as U.S. Pat. No. 9,060,776 on Jun. 23, 2015, the disclosure of which is incorporated by reference herein. Other suitable configurations for power source (102) and controller (104) will be apparent to those of ordinary skill in the art in view of the teachings herein.

As best seen in FIG. 9, the lower side of first jaw (182) includes a longitudinally extending recess (197) adjacent to slot (183); while the upper side of second jaw (184) includes a longitudinally extending recess (193) adjacent to slot (185). FIG. 2 shows the upper side of first jaw (182) including a plurality of teeth serrations (188). It should be understood that the lower side of second jaw (184) may include complementary serrations that nest with serrations (188), to enhance gripping of tissue captured between jaws (182, 184) without necessarily tearing the tissue. Of course, serrations (188) may take any other suitable form or may be simply omitted altogether. It should also be understood that serrations (188) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (182, 184).

With jaws (182, 184) in a closed position, shaft assembly (160) and end effector (180) are sized and configured to fit through trocars having various inner diameters, such that instrument (100) is usable in minimally invasive surgery, though of course instrument (100) could also be used in open procedures if desired. By way of example only, with jaws (182, 184) in a closed position, shaft assembly (160) and end effector (180) may present an outer diameter of approximately 5 mm. Alternatively, shaft assembly (160) and end effector (180) may present any other suitable outer diameter (e.g., between approximately 2 mm and approximately 20 mm, etc.).

In some versions, end effector (180) includes one or more sensors (not shown) that are configured to sense a variety of parameters at end effector (180), including but not limited to temperature of adjacent tissue, electrical resistance or impedance of adjacent tissue, voltage across adjacent tissue, forces exerted on jaws (182, 184) by adjacent tissue, etc. By way of example only, end effector (180) may include one or more positive temperature coefficient (PTC) thermistor bodies (189) (e.g., PTC polymer, etc.), located adjacent to electrodes (186, 187) and/or elsewhere. Data from sensors may be communicated to controller (104). Controller (104) may process such data in a variety of ways. By way of example only, controller (104) may modulate or otherwise change the RF energy being delivered to electrode surface (186, 187), based at least in part on data acquired from one or more sensors at end effector (180). In addition or in the alternative, controller (104) may alert the user to one or more conditions via an audio and/or visual feedback device (e.g., speaker, lights, display screen, etc.), based at least in part on data acquired from one or more sensors at end effector (180). It should also be understood that some kinds of sensors need not necessarily be in communication with controller (104), and may simply provide a purely localized effect at end effector (180). For instance. PTC thermistor bodies (189) at end effector (180) may automatically reduce the energy delivery at electrode surface (186, 187) as the temperature of the tissue and/or end effector (180) increases, thereby reducing the likelihood of overheating. In some such versions, a PTC thermistor element is in series with power source (102) and electrode surface (186, 187); and the PTC thermistor provides an increased impedance (reducing flow of current) in response to temperatures exceeding a threshold. Furthermore, it should be understood that electrode surface (186, 187) may be used as sensors (e.g., to sense tissue impedance, etc.). Various kinds of sensors that may be incorporated into instrument (100) will be apparent to those of ordinary skill in the art in view of the teachings herein. Similarly various things that can be done with data from sensors, by controller (104) or otherwise, will be apparent to those of ordinary skill in the art in view of the teachings herein. Other suitable variations for end effector (180) will also be apparent to those of ordinary skill in the art in view of the teachings herein.

Firing beam (190) is longitudinally movable along part of the length of end effector (180). Firing beam (190) is coaxially positioned within shaft assembly (160), extends along part of the length of shaft assembly (160), and translates longitudinally within shaft assembly (160) (including articulation section (170) in the present example), though it should be understood that firing beam (190) and shaft assembly (160) may have any other suitable relationship. As shown in FIG. 6, firing beam (190) is secured to a firing block (168), such that firing beam (190) and firing block (168) translate unitarily together within sheath (162). Firing block (168) is secured to firing tube (167), which is best seen in FIG. 5. Firing block (168) and firing tube (167) translate unitarily together within sheath (162). Firing beam coupling (166) is secured to firing tube (167), such that translating firing beam coupling (166) will translate firing beam (190) through the above-described couplings.

Firing beam (190) includes a sharp distal blade (194), an upper flange (192), and a lower flange (196). As best seen in FIGS. 8-9, distal blade (194) extends through slots (183, 185) of jaws (182, 184), with upper flange (192) being located above jaw (184) in recess (59) and lower flange (196) being located below jaw (182) in recess (58). The configuration of distal blade (194) and flanges (62, 66) provides an "I-beam" type of cross section at the distal end of firing beam (190). While flanges (192, 196) extend longitudinally only along a small portion of the length of firing beam (190) in the present example, it should be understood that flanges (192, 196) may extend longitudinally along any suitable length of firing beam (190). In addition, while flanges (192, 196) are positioned along the exterior of jaws (182, 184), flanges (192, 196) may alternatively be disposed in corresponding slots formed within jaws (182, 184). For instance, each jaw (182, 184) may define a 'T'-shaped slot, with parts of distal blade (194) being disposed in one vertical portion of each 'T'-shaped slot and with flanges (192, 196) being disposed in the horizontal portions of the "T"-shaped slots. Various other suitable configurations and relationships will be apparent to those of ordinary skill in the art in view of the teachings herein.

Distal blade (194) is substantially sharp, such that distal blade (194) will readily sever tissue that is captured between jaws (182, 184). Distal blade (194) is also electrically grounded in the present example, providing a return path for RF energy as described elsewhere herein. In some other versions, distal blade (194) serves as an active electrode. In addition or in the alternative, distal blade (194) may be selectively energized with ultrasonic energy (e.g., harmonic vibrations at approximately 55.5 kHz, etc.).

The "I-beam" type of configuration of firing beam (190) provides closure of jaws (182, 184) as firing beam (190) is advanced distally. In particular, flange (192) urges jaw (184) pivotally toward jaw (182) as firing beam (190) is advanced from a proximal position to a distal position, by bearing against recess (193) formed in jaw (184). This closing effect on jaws (182, 184) by firing beam (190) may occur before distal blade (194) reaches tissue captured between jaws (182, 184). Such staging of encounters by firing beam (190) may reduce the force required to actuate firing beam (190) distally through a full firing stroke. In other words, in some such versions, firing beam (190) may have already overcome an initial resistance required to substantially close jaws (182, 184) on tissue before encountering resistance from severing the tissue captured between jaws (182, 184). Of course, any other suitable staging may be provided.

In the present example, flange (192) is configured to cam against a ramp feature at the proximal end of jaw (184) to open jaw (184) when firing beam (190) is retracted to a proximal position and to hold jaw (184) open when firing beam (190) remains at the proximal position. This camming capability may facilitate use of end effector (180) to separate layers of tissue, to perform blunt dissections, etc., by forcing jaws (182, 184) apart from a closed position. In some other versions, jaws (182, 184) are resiliently biased to an open position by a spring or other type of resilient feature. While jaws (182, 184) close or open as firing beam (190) is translated in the present example, it should be understood that other versions may provide independent movement of jaws (182, 184) and firing beam (190). By way of example only, one or more cables, rods, beams, or other features may extend through shaft assembly (160) to selectively actuate jaws (182, 184) independently of firing beam (190).

C. Exemplary Robotic Arm Interface Assembly

FIGS. 4 and 10-13 show interface assembly (110) of the present example in greater detail. As shown, interface assembly (110) comprises a housing (112), a base (114), and a cable (118). Housing (112) comprises a shell that simply encloses drive components. In some versions, housing (112) also includes an electronic circuit board, chip, and/or other feature that is configured to identify instrument (100). Such identification may be carried out through cable (118). Cable (118) is configured to couple with power source (102) and controller (104). A strain relief (119) is provided at the interface of cable (118) and housing (112). It should be noted that housing (112) is omitted from FIGS. 11-13 for the sake of clarity.

Figure 10:
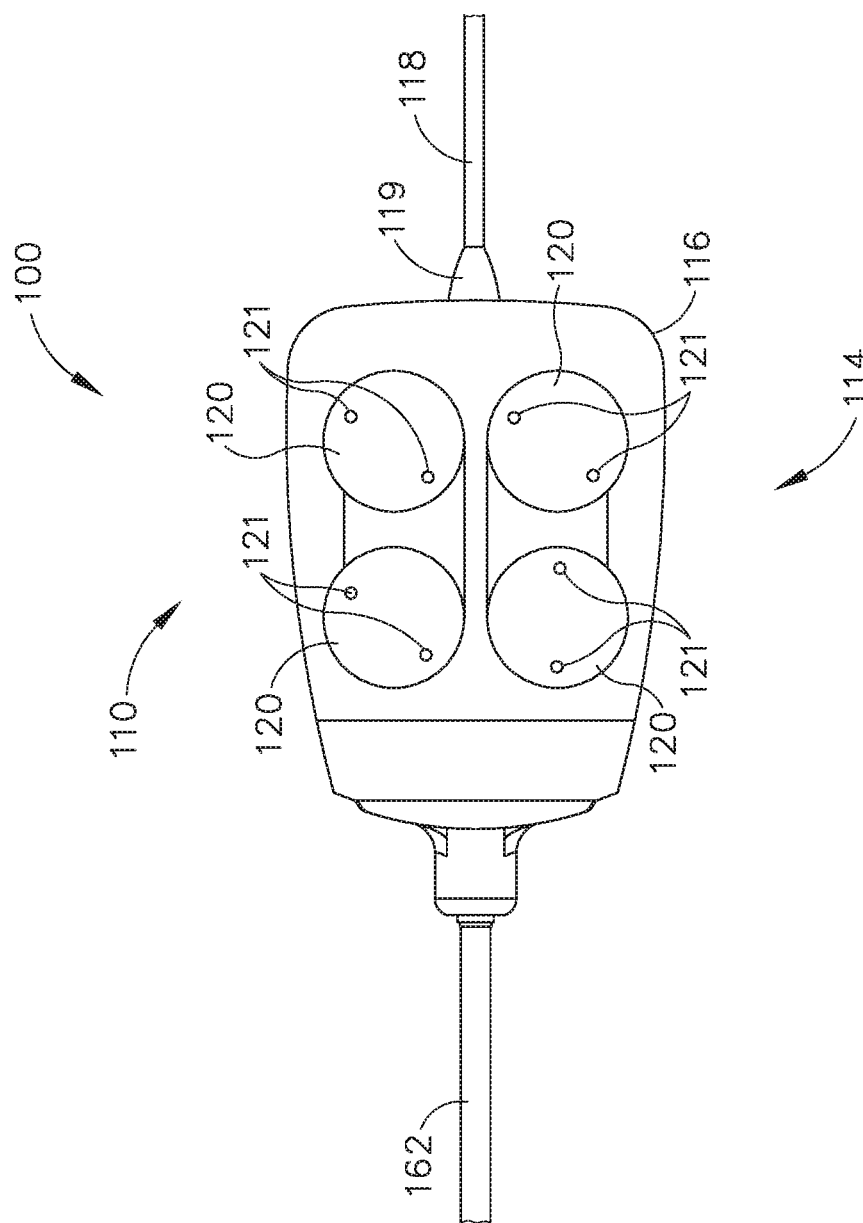
FIG. 10 depicts a bottom plan view of a proximal portion of the instrument of FIG. 4.
Figure 11:
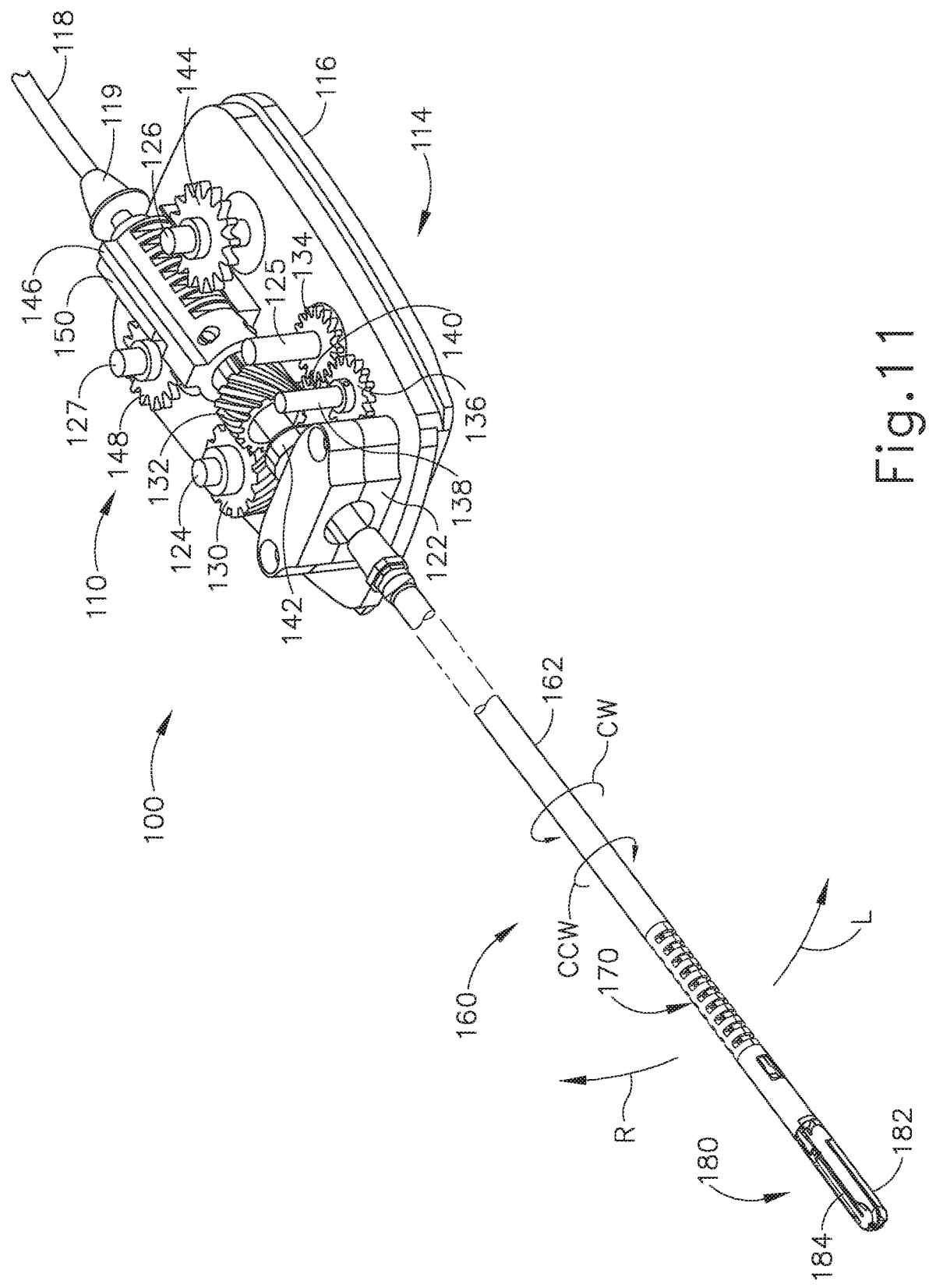
FIG. 11 depicts a perspective view of the instrument of FIG. 4, with a top cover removed.
Figure 12:
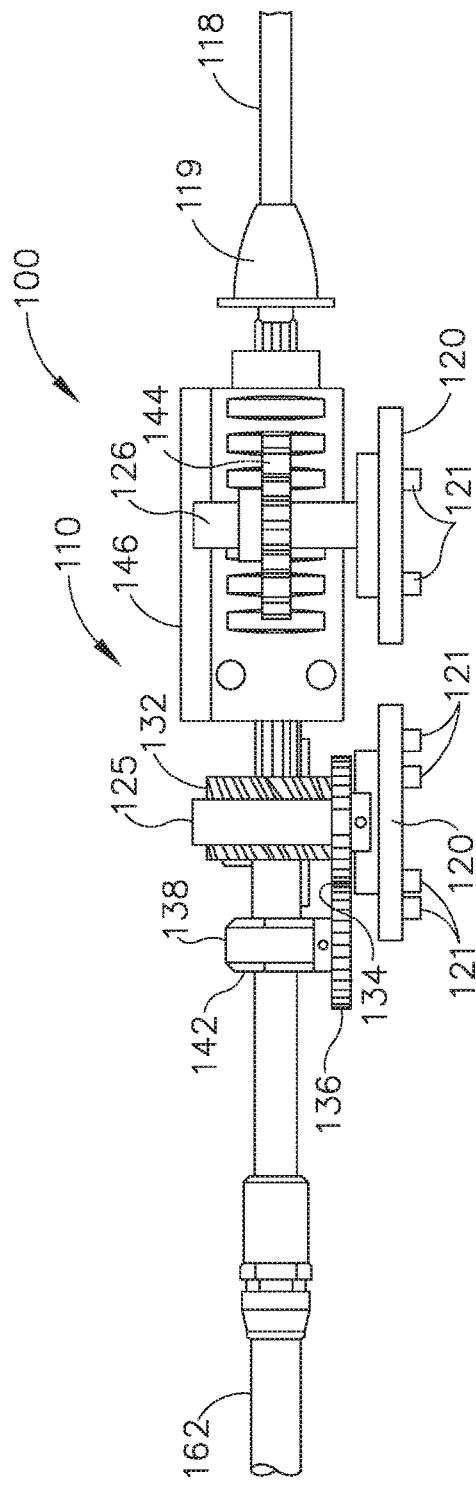
FIG. 12 depicts a left side elevational view of the instrument of FIG. 4, with the top cover removed.
Figure 13:
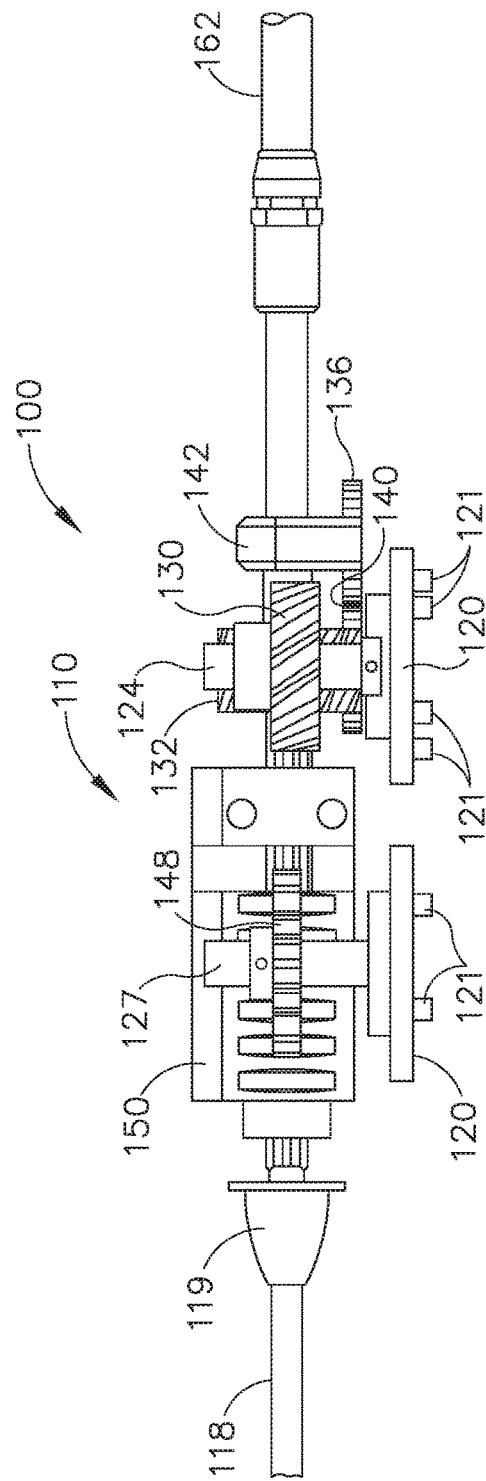
FIG. 13 depicts a right side elevational view of the instrument of FIG. 4, with the top cover removed.

Base (114) includes a mounting plate (116) that engages dock (72) of robotic arm cart (40). It should be noted that plate (116) is omitted from FIGS. 12-13 for the sake of clarity. While not shown, it should be understood that base (114) may also include one or more electrical contacts and/or other features operable to establish electrical communication with a complementary feature of dock (72). A shaft support structure (122) extends upwardly from base (114) and provides support to shaft assembly (160) (while still allowing shaft assembly (160) to rotate). By way of example only, shaft support structure (122) may include a busing, bearings, and/or other features that facilitate rotation of shaft assembly (160) relative to support structure (122). As shown in FIG. 10, base (114) further includes four drive discs (120) that are rotatable relative to plate (116). Each disc (120) includes a pair of unitary pins (121) that couple with complementary recesses (not shown) in drive elements of dock (72). In some versions, one pin (121) of each pair is closer to the axis of rotation of the corresponding disc (120), to ensure proper angular orientation of disc (120) relative to the corresponding drive element of dock (72). As best seen in FIGS. 11-13, a drive shaft (124, 125, 126, 127) extends unitarily upwardly from each disc (120). As will be described in greater detail below, discs (120) are operable to provide independent rotation of shaft assembly (160), bending of articulation section (170), and translation of firing beam (190), through rotation of drive shafts (124, 125, 126, 127).

As best seen in FIG. 11, a first helical gear (130) is fixedly secured to drive shaft (124), such that rotation of the corresponding disc (120) provides rotation of first helical gear (130). First helical gear (130) meshes with a second helical gear (132), which is fixedly secured to rotary coupling (164). Thus, rotation of first helical gear (130) provides rotation of shaft assembly (160). It should be understood that rotation of first helical gear (130) about a first axis is converted into rotation of second helical gear (132) about a second axis, which is orthogonal to the first axis. A clockwise (CW) rotation of second helical gear (132) results in CW rotation of shaft assembly (160). A counter-clockwise (CCW) rotation of second helical gear (132) results in CCW rotation of shaft assembly (160). Other suitable ways in which shaft assembly (160) may be rotated will be apparent to those of ordinary skill in the art in view of the teachings herein.

As best seen in FIGS. 11-12, a spur gear (134) is fixedly secured to drive shaft (125), such that rotation of the corresponding disc (120) provides rotation of spur gear (134). Spur gear (134) meshes with a first spur pinion (136), which is fixedly secured to a pinion shaft (138). Pinion shaft (138) is supported by base (116) and rotates freely relative to base (116), such that first spur pinion (136) is rotatable as an idler. It should therefore be understood that first spur pinion (136) rotates in response to rotation of spur gear (134). First spur pinion (136) also meshes with a rack (140), which is fixedly secured to a drive block (142). Drive block (142) is secured to firing beam coupling (166). Thus, rotation of first spur pinion (136) is converted to translation of firing beam (190) via rack (140), drive block (142), and firing beam coupling (166). As noted above, firing beam (190) is operable to first close jaws (182, 184) together about tissue during a first range of distal travel of firing beam (190); then sever the tissue clamped between jaws (182, 184) during a first range of distal travel of firing beam (190). Thus tissue may be clamped and severed by rotation of drive shaft (125) via its corresponding disc (120). When this rotation is reversed, firing beam (190) retracts proximally, ultimately opening jaws (182, 184) to release tissue. Other suitable ways in which firing beam (190) may be translated will be apparent to those of ordinary skill in the art in view of the teachings herein.

With respect to articulation control, FIGS. 11-12 show a second spur pinion (144) fixedly secured to drive shaft (126), such that rotation of the corresponding disc (120) provides rotation of second spur pinion (144). Second spur pinion (144) meshes with a left rack (146), which is fixedly secured to articulation beam (174). It should be understood that articulation beam (174) will translate distally or proximally in response to rotation of drive shaft (126). Similarly, FIGS. 11 and 13 show a third spur pinion (148) fixedly secured to drive shaft (127), such that rotation of the corresponding disc (120) provides rotation of third spur pinion (148). Third spur pinion (148) meshes with a right rack (150), which is fixedly secured to articulation beam (176). It should be understood that articulation beam (176) will translate distally or proximally in response to rotation of drive shaft (127).

It should also be understood that drive shafts (126, 127) may be rotated in the same direction simultaneously in order to provide opposing translation of beams (174, 176). For instance, drive shaft (126) may be rotated clockwise to retract beam (174) proximally, with drive shaft (127) being rotated clockwise to advance beam (176) distally, to thereby deflect end effector (180) to the left (L) at articulation section (170). Conversely, drive shaft (126) may be rotated counter-clockwise to advance beam (174) distally, with drive shaft (127) being rotated counter-clockwise to retract beam (176) proximally, to deflect end effector (180) to the left (R) at articulation section (170). Other suitable ways in which end effector (180) may be articulated at articulation section (170) will be apparent to those of ordinary skill in the art in view of the teachings herein. By way of example only, articulation control may be provided in accordance with at least some of the teachings of U.S. Pub. No. 2012/0078243, issued as U.S. Pat. No. 9,877,720, the disclosure of which is incorporated by reference herein; and/or U.S. Pub. No. 2013/0023868, issued as U.S. Pat. No. 9,545,253, the disclosure of which is incorporated by reference herein. It should also be understood that some versions of instrument (100) may simply lack an articulation section (170) and corresponding control.

D. Exemplary Operation

In an exemplary use, arm cart (40) is used to insert end effector (180) into a patient via a trocar. Articulation section (170) is substantially straight when end effector (180) and part of shaft assembly (160) are inserted through the trocar. Drive shaft (124) may be rotated through drive features in dock (72) that are coupled with the corresponding disc (120), to position end effector (180) at a desired angular orientation relative to the tissue. Drive shafts (126, 126) may then be rotated through drive features in dock (72) that are coupled with the corresponding discs (120), to pivot or flex articulation section (170) of shaft assembly (160) in order to position end effector (180) at a desired position and orientation relative to an anatomical structure within the patient. Two layers of tissue of the anatomical structure are then captured between jaws (182, 184) by rotating drive shaft (125) to advance firing beam (190) distally through a first range of motion. Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of instrument (100) is perpendicular to the longitudinal axis defined by end effector (180), etc.). In other words, the lengths of jaws (182, 184) may be oriented perpendicular to (or at least generally transverse to) the length of the blood vessel. As noted above, flanges (192, 196) cammingly act to pivot jaw (182) toward jaw (184) when firing beam (190) is actuated distally by rotating drive shaft (125).

With tissue layers captured between jaws (182, 184) firing beam (190) continues to advance distally in response to continued rotation of drive shaft (125). As firing beam (190) continues to advance distally, distal blade (194) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (192, 196) immediately above and below jaws (182, 184), respectively, may help keep jaws (182, 184) in a closed and tightly clamping position. In particular, flanges (192, 196) may help maintain a significantly compressive force between jaws (182, 184). With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). In some versions, electrodes (186, 187) are selectively coupled with power source (102) such that electrode surface (186, 187) of jaws (182, 184) are activated with a common first polarity while firing beam (190) is activated at a second polarity that is opposite to the first polarity. Thus, a bipolar RF current flows between firing beam (190) and electrode surfaces (186, 187) of jaws (182, 184), through the compressed regions of severed tissue layer portions. In some other versions, electrode surface (186) has one polarity while electrode surface (187) and firing beam (190) both have the other polarity. In either version (among at least some others), bipolar RF energy delivered by power source (102) ultimately thermally welds the tissue layer portions on one side of firing beam (190) together and the tissue layer portions on the other side of firing beam (190) together.

In certain circumstances, the heat generated by activated electrode surfaces (186, 187) can denature the collagen within the tissue layer portions and, in cooperation with clamping pressure provided by jaws (182, 184), the denatured collagen can form a seal within the tissue layer portions. Thus, the severed ends of the natural lumen defining anatomical structure are hemostatically sealed shut, such that the severed ends will not leak bodily fluids. In some versions, electrode surface (186, 187) may be activated with bipolar RF energy before firing beam (190) even begins to translate distally and thus before the tissue is even severed. Other suitable ways in which instrument (100) may be operable and operated will be apparent to those of ordinary skill in the art in view of the teachings herein.

Figure 14:
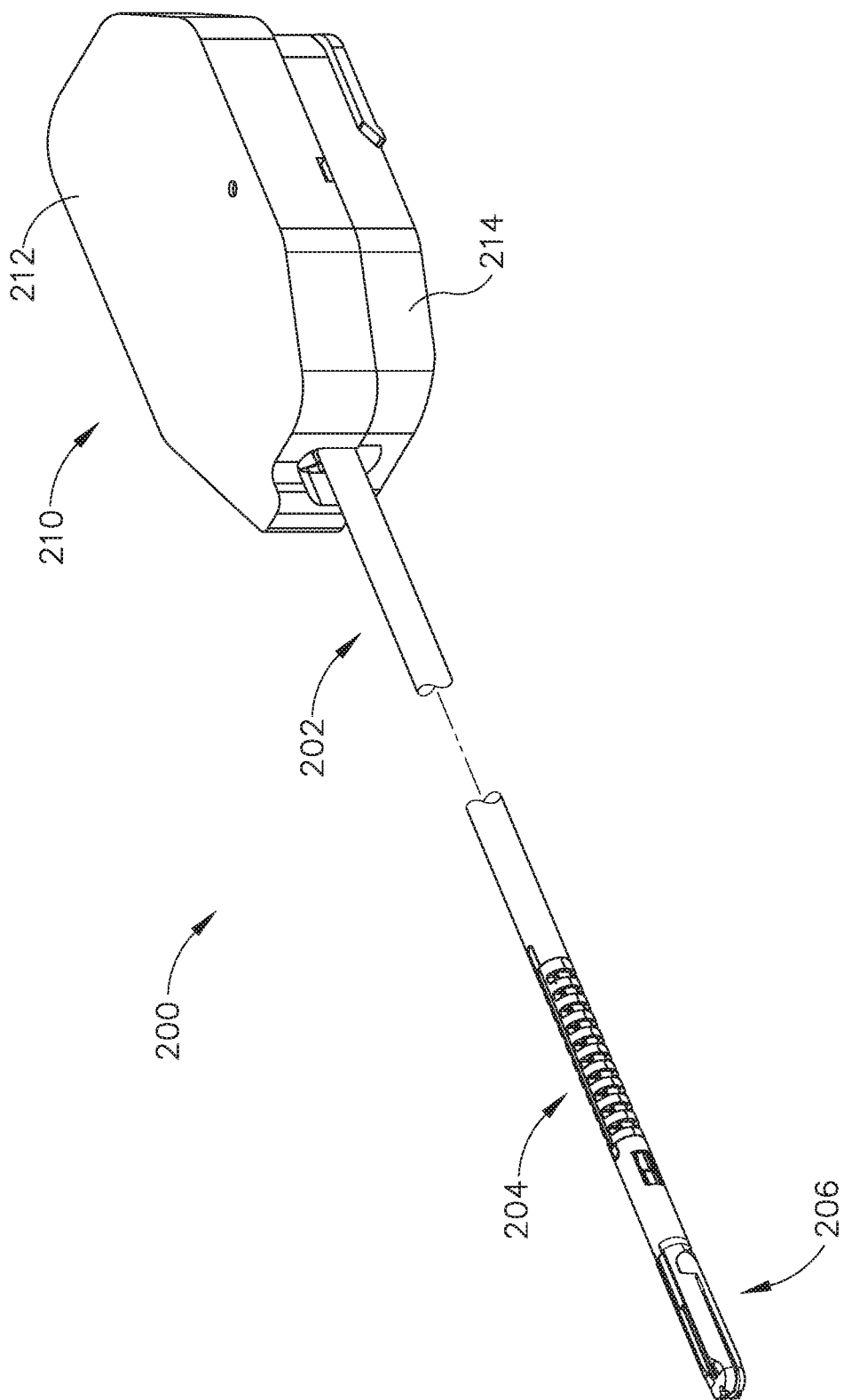
FIG. 14 depicts a top, perspective view of an exemplary alternative surgical instrument for incorporation with the system of FIG. 1.

III. Exemplary Alternative Electrosurgical Instrument with Articulation Feature and Separable Compartment FIG. 14 shows an exemplary alternative electrosurgical instrument (200). Instrument (200) of this example is substantially similar to instrument (100) described above in that instrument (200) has a shaft assembly (202), an articulation section (204), and an end effector (206) that are substantially identical to shaft assembly (160), articulation section (170), and end effector (180) described above. Instrument (200) of this example is also operable to couple with a dock (72) of robotic arm cart (40) via an interface assembly (210). However, interface assembly (210) of this example is different from interface assembly (110) described above.

Interface assembly (210) comprises a housing (212) and a base (214). Housing (212) is operable to snap against base (214), though it will be appreciated that any suitable means for connecting housing (212) and base (214) may be used as would be apparent to one of ordinary skill in the art. Interface assembly (210) further comprises a shaft cartridge (220), which may be seen in FIG. 15. Shaft cartridge (220) is positioned at the proximal end of shaft assembly (202). Furthermore, shaft cartridge (220) is sized such that housing (212) and base (214) may enclose shaft cartridge (220) completely.

Figure 18:
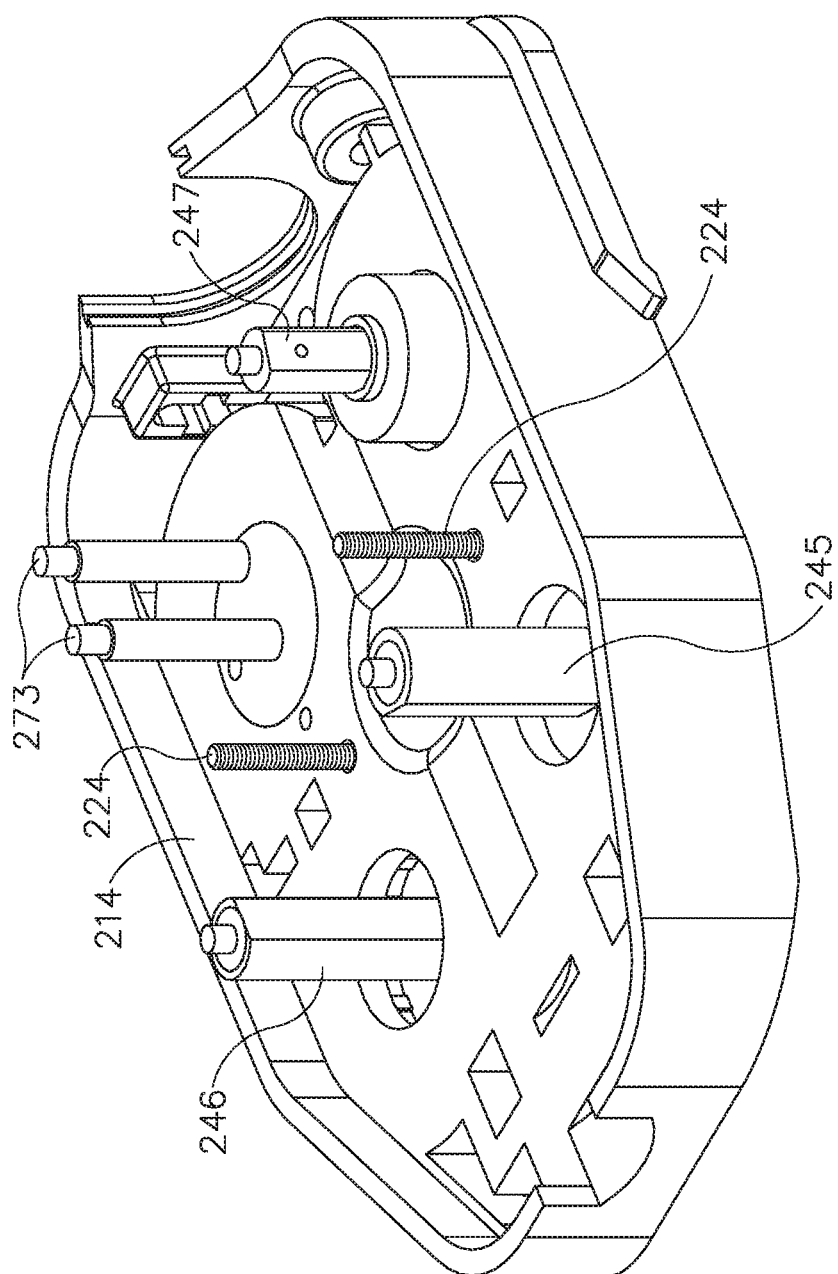
FIG. 18 depicts a top, perspective view of the base of the surgical instrument of FIG. 14.

Housing (212) is shaped as an upper clamshell-like structure for closing upon base (214) and holding a portion of shaft cartridge (220). Housing (212) comprises screw holes (221) operable to receive screws (224) from base (214), which are shown in FIG. 18. Housing (212) further comprises a half sleeve (222). Half sleeve (222) is shaped as a half pipe, but may have any suitable shape operable to receive a portion of shaft assembly (202). Half sleeve (222) comprises a slot (223) shaped to couple with shaft assembly (202) such that once shaft assembly (202) fits within half sleeve (222), the engagement between slot (223) and shaft assembly (202) prevents longitudinal motion of shaft assembly (202). However, half sleeve (222) allows shaft assembly (202) to rotate even though half sleeve (222) prevents translation of shaft assembly (202) relative to housing (212). It will be appreciated that that in some versions, slot (223) may be omitted entirely.

Figure 17:
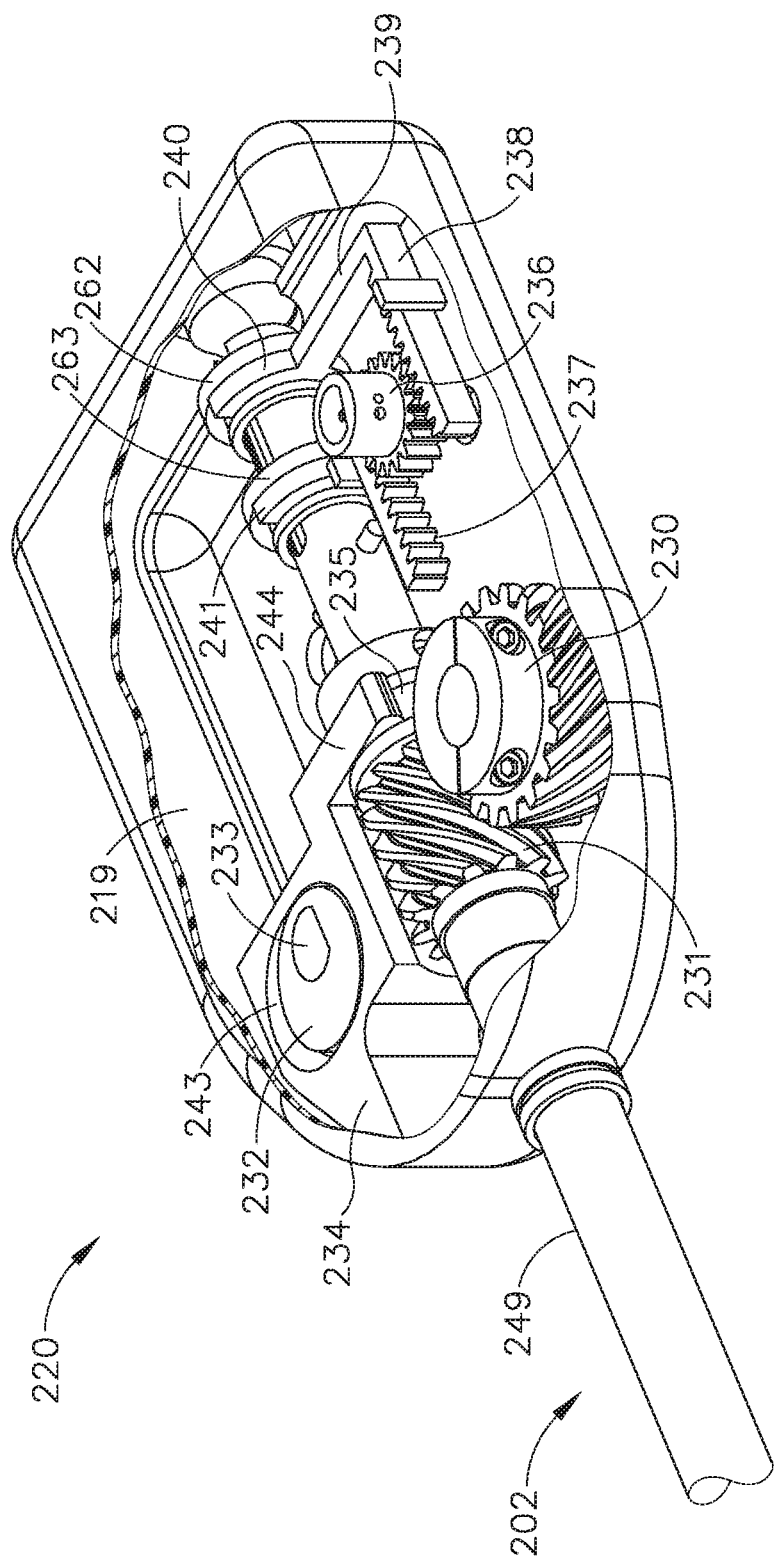
FIG. 17 depicts a top, perspective view of the separable compartment of the surgical instrument of FIG. 14, with a housing portion omitted to reveal internal components.

FIG. 17 shows shaft cartridge (220) with shaft assembly (202) extending outwardly from shaft cartridge (220). Shaft cartridge (220) includes a shell (219) operable to hold a variety of components, which will be discussed below and are contained fully within shell (219). Base (214) is operable to receive shaft cartridge (220). While the exemplary version contemplates shaft cartridge (220) holding shaft assembly (202), with shaft assembly (202) having an electrosurgical end effector (206), it will be appreciated that other suitable shaft cartridges (220) compatible with other types of end effectors may be used as well. For instance, in the alternative or in addition to an electrosurgical end effector (206), an ultrasonic end effector or a stapling end effector may be used. Other suitable end effectors for manipulating tissue may be used as would be apparent to one of ordinary skill in the art in view of the teachings herein. Shaft cartridge (220) comprises a first helical gear (230) that meshes with a shaft helical gear (231). Shaft helical gear (231) is unitarily coupled with tube (249) of shaft assembly (202) such that shaft helical gear (231) is operable to rotate shaft assembly (202).

Figure 19:
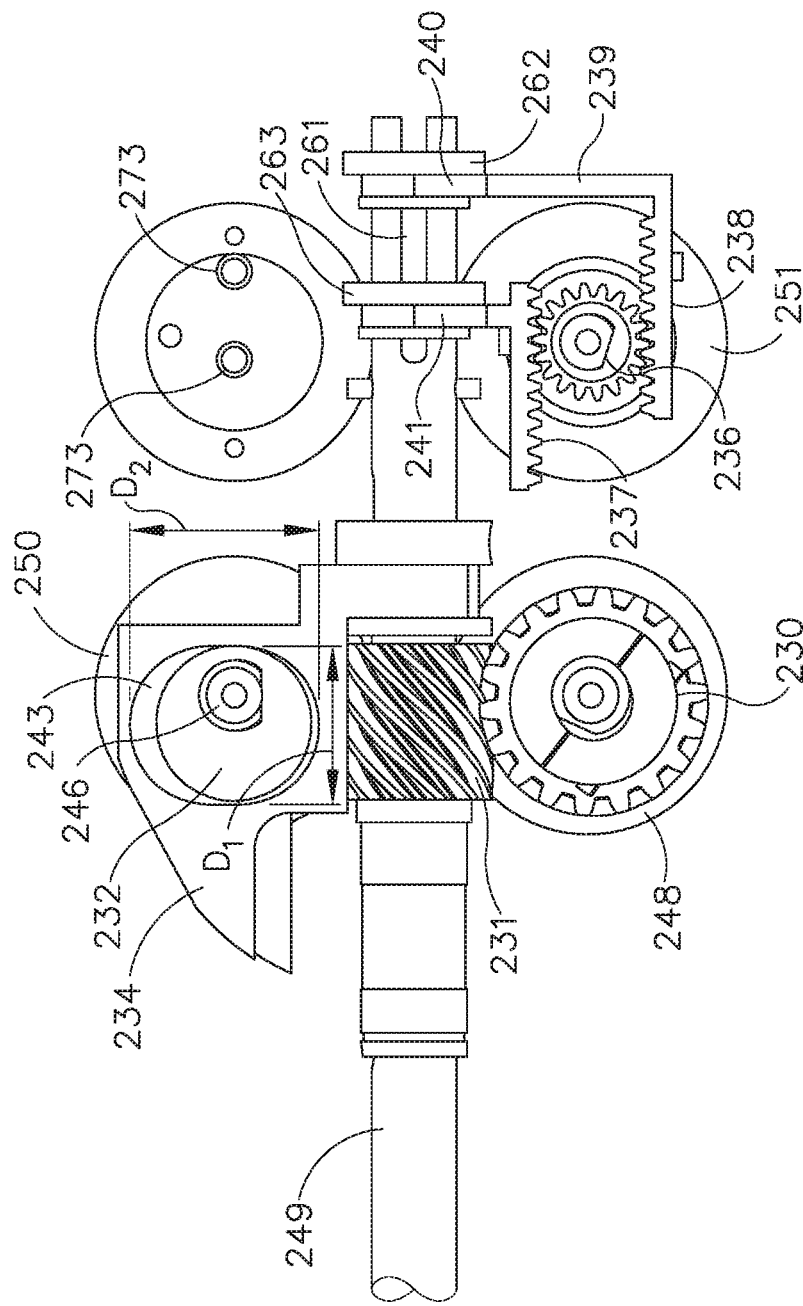
FIG. 19 depicts a top, plan view of the surgical instrument of FIG. 14, showing the drive shafts of the base engaging the internal portions of the separable compartment.

Shaft cartridge (220) further comprises a cam cylinder (232) and a drive block (234). Cam cylinder (232) defines a shaft opening (233) operable to receive a drive shaft as will be discussed in further detail below. Drive block (234) defines a cam opening (243) through which cam cylinder (232) extends. As seen in FIG. 19, cam opening (243) is shaped as an elongate slot. Cam opening (243) defines two diameters: D1 and D2. As seen in FIG. 19, cam cylinder (232) has roughly the same size diameter as D1, whereas cam cylinder (232) has a smaller diameter than D2. As a result, as cam cylinder (232) rotates within cam opening (243), drive block (234) oscillates back and forth longitudinally. Drive block (234) is in communication with holder (244) which is operable to grip shaft ring (235). Shaft ring (235) is able to freely rotate while being held by holder (244). As drive block (234) translates distally and proximally, shaft ring (235) also translates distally and proximally. It will be appreciated that shaft ring (235) may be coupled with a firing beam (190) such as one seen in FIG. 8. As a result, shaft ring (235) is operable to drive firing beam (190) longitudinally along shaft assembly (202).

Shaft cartridge (220) also comprises a spur gear (236), which meshes with a first rack (237) and a second rack (238). First rack (237) and second rack (238) are positioned on opposing sides of spur gear (236). First rack (237) includes an integral first clip (241), which is secured to a first drive ring (263) as will be described in greater detail below. Second rack (238) includes an integral second clip (240) at the end of an integral rack arm (239). Second clip (240) is secured to a second drive ring (262) as will be described in greater detail below. When spur gear (236) rotates, first rack (237) and second rack (238) move in opposing longitudinal directions. As a result, rotation of spur gear (236) in one direction causes first clip (241) and second clip (240) to spread apart whereas rotation in the opposite direction causes first clip (241) and second clip (240) to translate toward each other. It will be appreciated that spur gear (236), first helical gear (230), and cam cylinder (232) are operable to engage a plurality of drive shafts which will be discussed below.

FIG. 18 shows base (214), which comprises a first drive shaft (245), a second drive shaft (246), and a third drive shaft (247). Base (214) further comprises free shafts (273). Free shafts (273) in the present example extend upwardly, perpendicularly away from base (214). Free shafts (273) do not rotate and are not configured to drive any portion of interface assembly (220). Drive shafts (245, 246, 247) also extend upwardly and are aligned generally with shaft cartridge (220). In particular, first drive shaft (245) is aligned with first helical gear (230), second drive shaft (246) is aligned with shaft opening (233), and third drive shaft (247) is aligned with spur gear (236). As a result, when shaft cartridge (220) is joined with base (214), first drive shaft (245) engages first helical gear (230), second drive shaft (246) engages shaft opening (233), and third drive shaft (247) engages spur gear (236). When second drive shaft (246) engages shaft opening (233), shaft opening (233) and second drive shaft (246) are offset from the longitudinal axis of cam cylinder (232). As a result, cam cylinder (232) is operable to rotate eccentrically in relation to drive block (234). FIG. 19 depicts drive features of base (214) joined with shaft cartridge (220), though shell (219) and the outer housing of base (214) have been removed for visibility purposes.

Drive shafts (245, 246, 247) are in communication with a plurality of drive plates (248, 250, 251). First drive shaft (245) connects to first drive plate (248), second drive shaft (246) connects to second drive plate (250), and third drive shaft (247) connects to third drive plate (251). Drive plates (248, 250, 251) may be coupled with, for example, drive discs (120) of FIG. 10. Drive discs (120) are operable to rotate drive plates (248, 250, 251), thereby controlling and rotating drive shafts (245, 246, 247).

Figure 20:
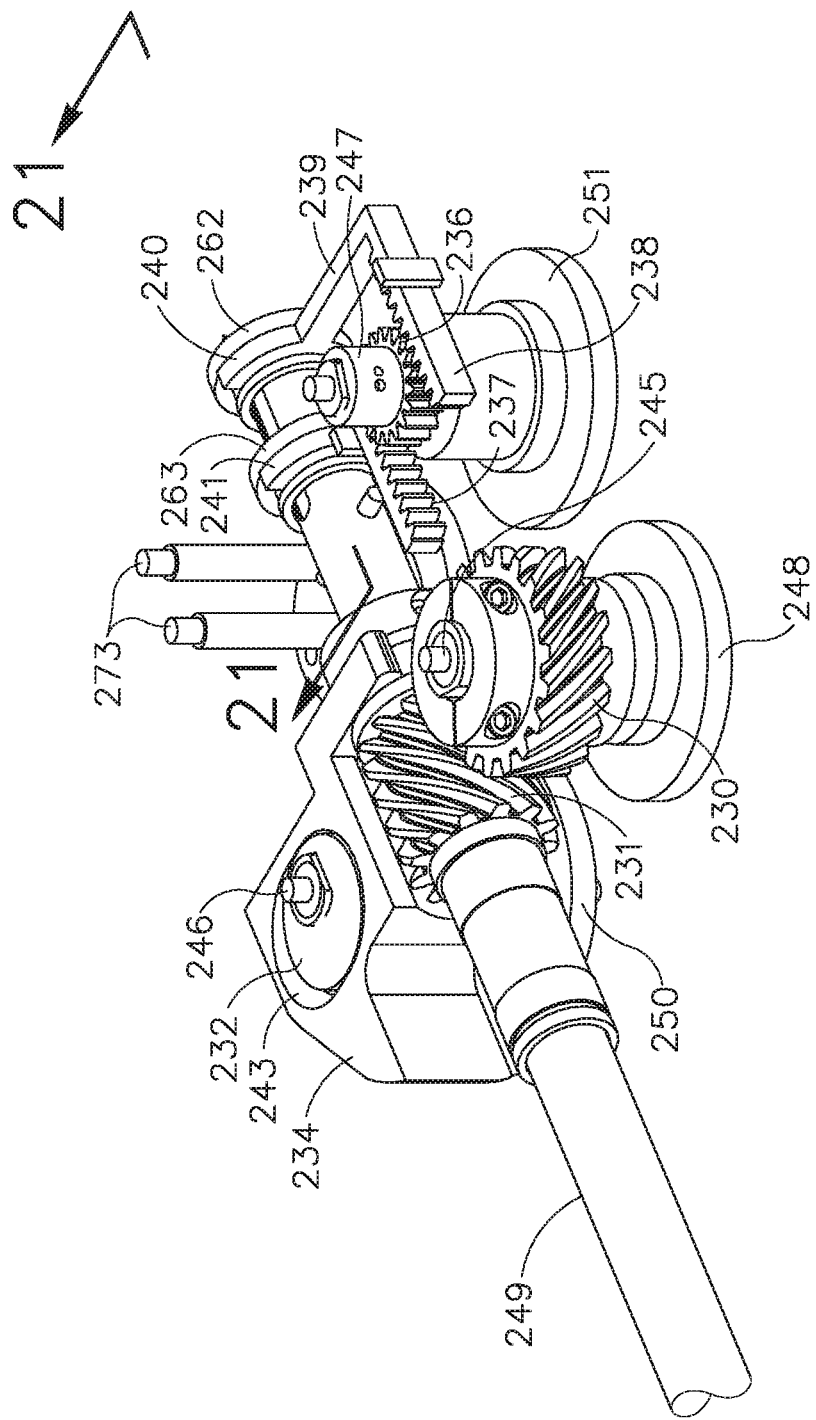
FIG. 20 depicts a top, perspective view of the surgical instrument of FIG. 14, showing the drive shafts of the base engaging the internal portions of the separable compartment.

As can been seen in FIG. 20, rotating first drive plate (248) is operable to rotate first helical gear (230), which turns shaft helical gear (231), which rotates tube (249) of shaft assembly (202). It will be understood that first drive plate (248) may be independently driven, and the resultant turning of shaft assembly (202) may be operable to rotate end effector (206). Rotating second drive plate (250) is operable to actuate drive block (234) such that a firing beam may be driven longitudinally through shaft assembly (202). Finally, rotating third drive plate (251) is operable to drive first clip (241) and second clip (240) longitudinally toward each other or to spread them apart longitudinally. In particular, spur gear (236) causes first rack (237) and second rack (238) to move in opposing directions to spread first clip (241) and second clip (240) apart or to drive clips (240, 241) toward each other longitudinally.

Figure 21:
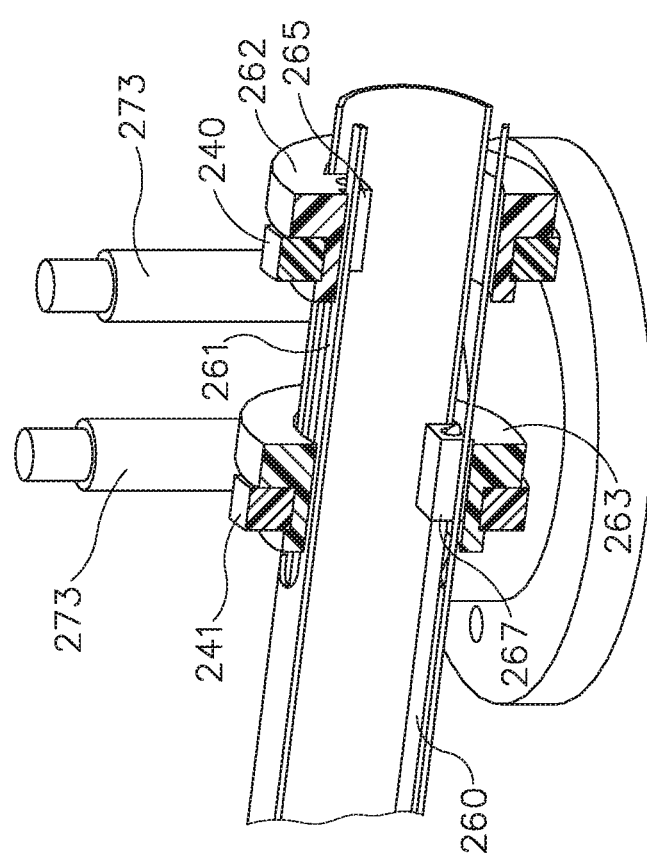
FIG. 21 depicts a perspective, cross sectional view of the shaft assembly of FIG. 14, taken along the line 21-21 of FIG. 20.

Moving to FIG. 21, as first clip (241) and second clip (240) translate toward or away from each other, first clip (241) and second clip (240) push and pull first articulation beam (260) and second articulation beam (261), respectively, within tube (249). First articulation beam (260) is secured to an integral anchor block (267) of drive ring (263). As noted above, clip (241) is secured to drive ring (263). Thus, first articulation beam (260) will translate longitudinally with clip (241). Similarly, second articulation beam (261) is secured to an integral anchor block (265) of drive ring (262). As noted above, clip (240) is secured to drive ring (262). Thus, second articulation beam (261) will translate longitudinally with clip (240). Thus, as first clip (241) and second clip (240) translate toward each other, first articulation beam (260) retracts proximally, longitudinally along tube (249) while second articulation beam (261) advances distally, longitudinally along tube (249). When first clip (241) and second clip (240) move apart from each other, first articulation beam (260) advances distally, longitudinally along tube (249) while second articulation beam (261) retracts proximally, longitudinally along tube (249). It will be appreciated that this pushing and pulling of articulation beams (260, 261) is communicated to articulation section (204) to effectuate articulation of end effector (206).

Figure 22:
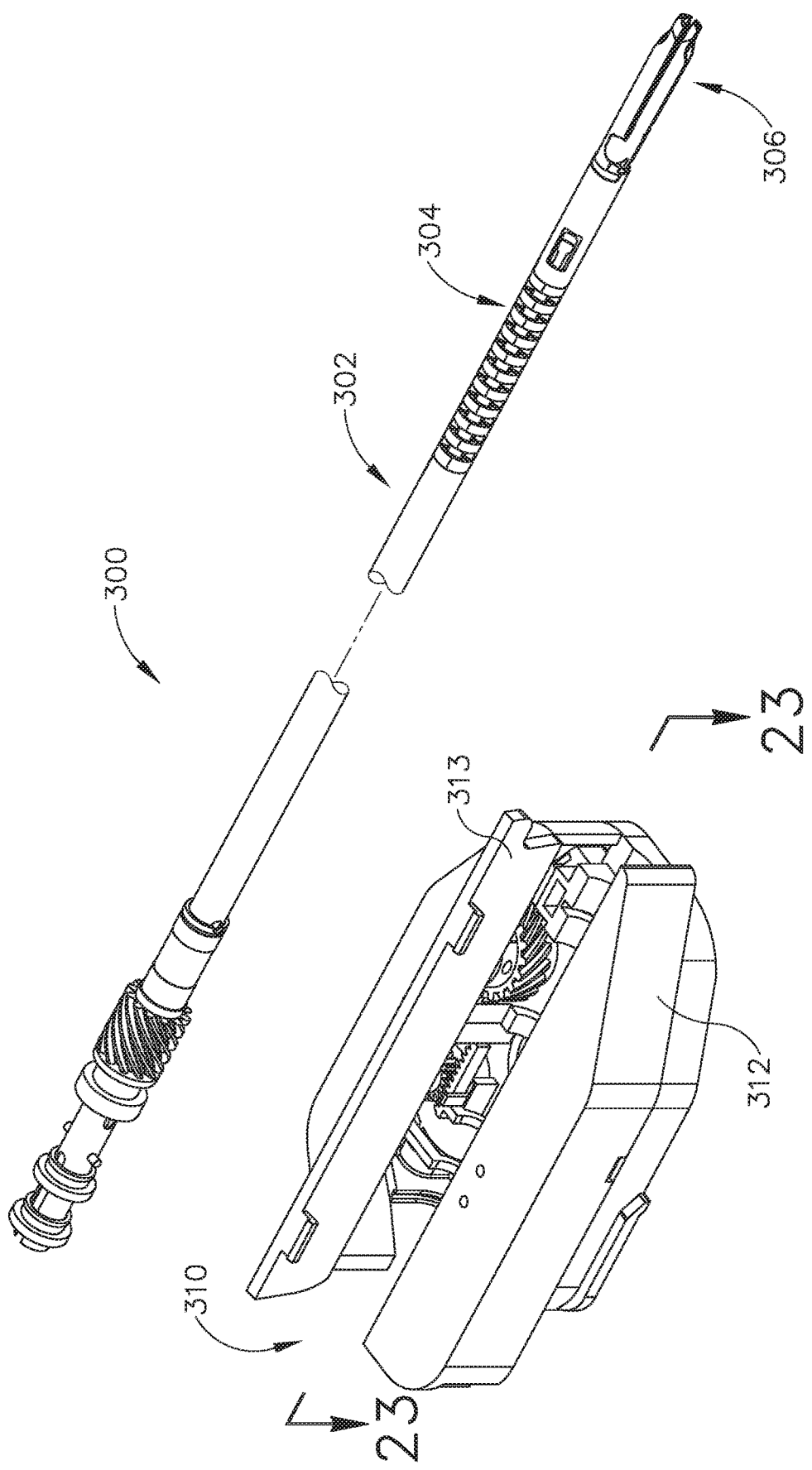
FIG. 22 depicts a top, perspective view of an exemplary alternative surgical instrument for incorporation with the system of FIG. 1, with a housing with a door.

IV. Exemplary Alternative Electrosurgical Instrument with Articulation Feature and Removable Interface Assembly Housing FIG. 22 shows an exemplary alternative electrosurgical instrument (300). Instrument (300) of this example is substantially similar to instrument (100) described above in that instrument (300) has a shaft assembly (302), an articulation section (304), and an end effector (306) that are substantially identical to shaft assembly (160), articulation section (170), and end effector (180) described above. Instrument (300) of this example is also operable to couple with a dock (72) of robotic arm cart (40) via an interface assembly (310).

Figure 23:
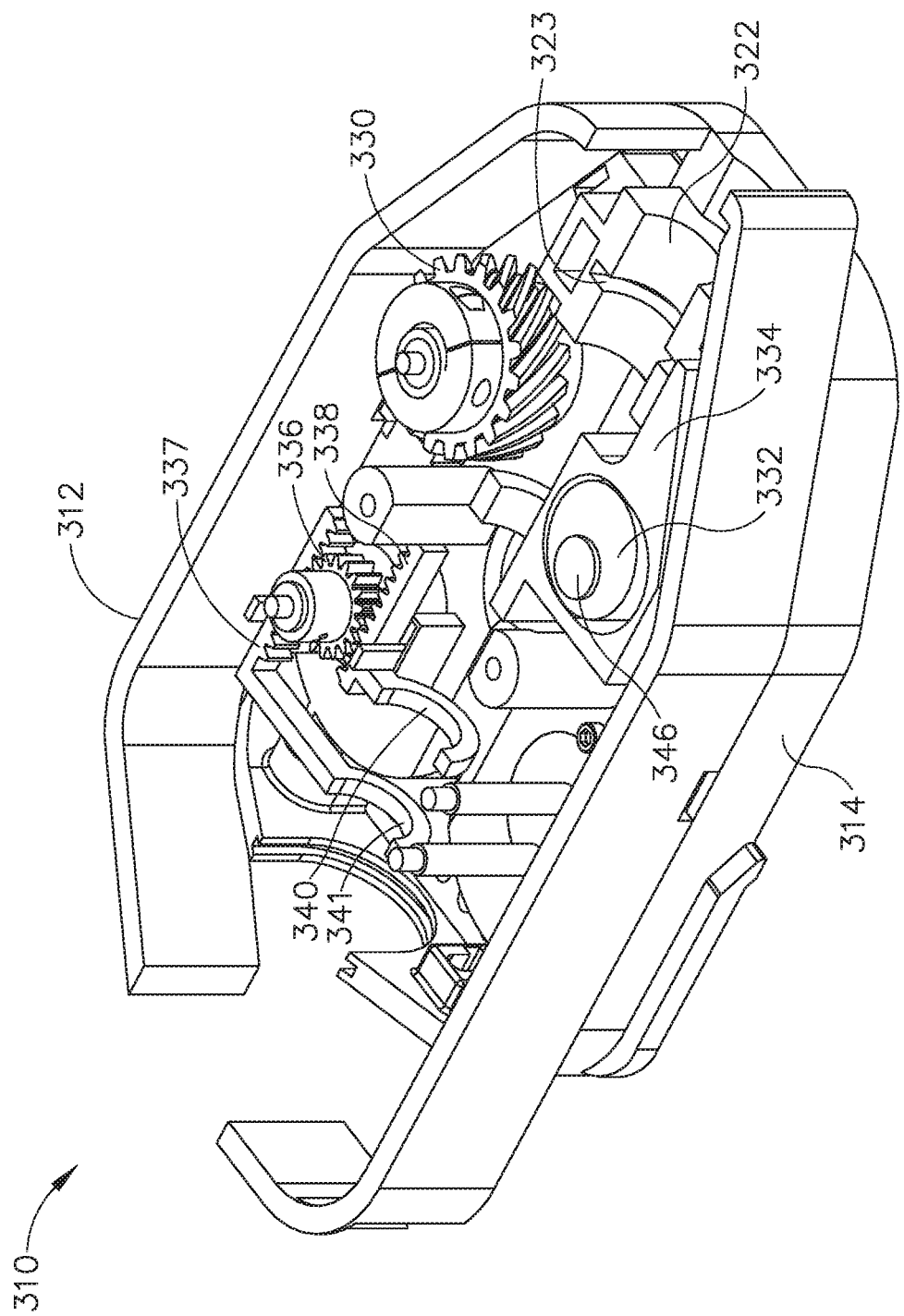
FIG. 23 depicts a top, perspective, cross sectional view of the surgical instrument of FIG. 22, taken along the line 23-23 of FIG. 22.

A cross sectional view of interface assembly (310) can be seen in FIG. 23. Interface assembly (310) comprises a housing (312), a base (314), and a door (313) (seen in FIG. 22). Door (313) is sized such that shaft assembly (302) is operable to fit through door (313) and fit within housing (312). Once shaft assembly (302) is placed in interface assembly (310), door (313) is operable to pivot to a closed position (not shown), thereby enclosing the proximal portion of shaft assembly (302) in interface assembly (310). While the exemplary version shows door (313) as being a hinged door, it will be appreciated that any suitable opening mechanism may be used as would be apparent to one of ordinary skill in the art. For instance, door (313) may comprise a sliding door, a snap-on door, or any other suitable door structure. Furthermore, while door (313) is positioned generally in the center, top of housing (312), door (313) may be positioned at any suitable location along housing (312). Furthermore, door (313) may be larger than shown in FIG. 22. Indeed, door (313) may be larger or smaller so long as door (313) can accommodate shaft assembly (302). Housing (312) comprises a half sleeve (222). Half sleeve (322) is shaped as a half pipe, but may have any suitable shape operable to receive a portion of shaft assembly (302). Half sleeve (322) comprises a slot (323) shaped to couple with engagement ring (370) (seen in FIG. 24) of shaft assembly (302) such that once shaft assembly (302) fits within half sleeve (322), the engagement between slot (323) and engagement ring (370) prevents longitudinal motion of shaft assembly (302). However, half sleeve (322) allows shaft assembly (302) to rotate even though half sleeve (322) prevents translation of shaft assembly (302) relative to housing (312). It will be appreciated that that in some versions, slot (323) may be omitted entirely.

Figure 24:
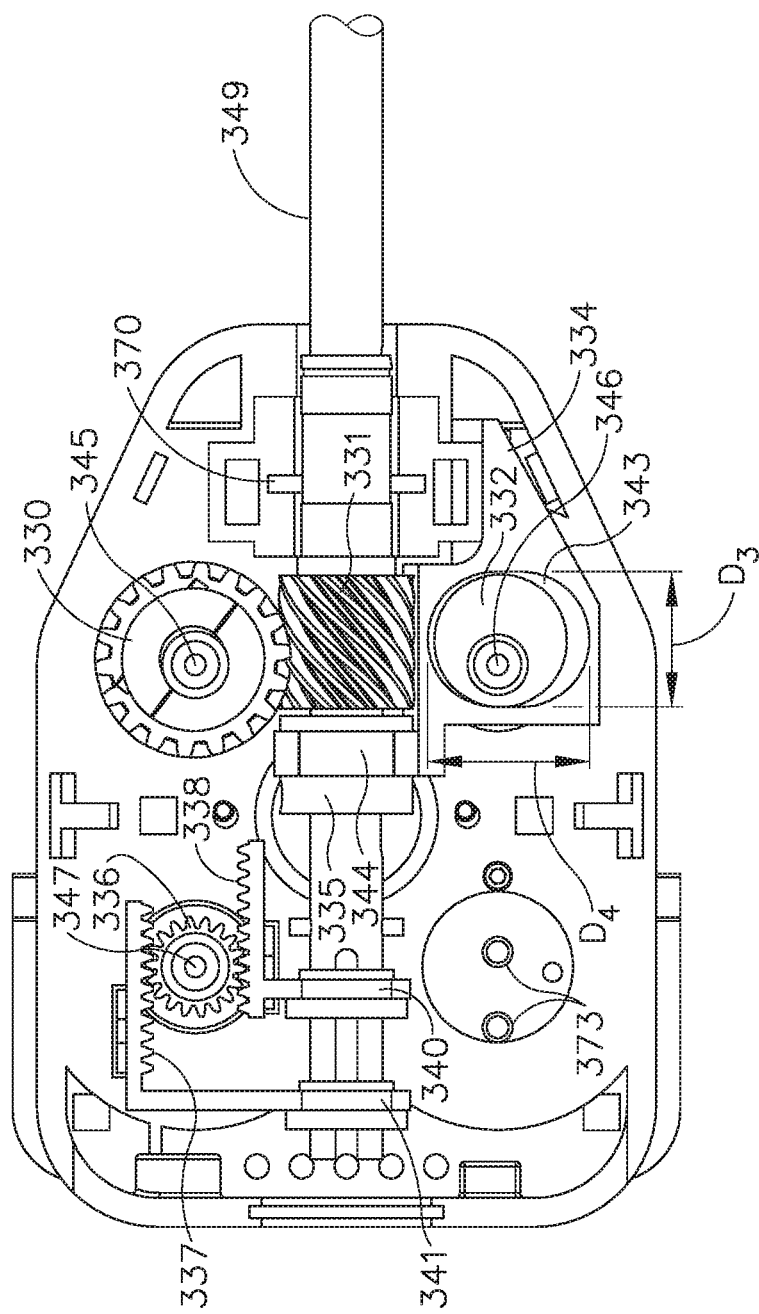
FIG. 24 depicts a top, plan view of the surgical instrument of FIG. 22 with the housing removed.

FIG. 24 shows shaft assembly (302) extending outwardly from housing (312). Shaft assembly (302) comprises a first helical gear (330) that meshes with a shaft helical gear (331). It will be appreciated that first helical gear (330) and shaft helical gear (331) are substantially similar to first helical gear (230) and shaft helical gear (231) of FIG. 17. Shaft helical gear (331) is unitarily coupled with tube (349) of shaft assembly (302) such that driving shaft helical gear (331) is operable to rotate shaft assembly (302).

Housing (312) further comprises a cam cylinder (332) and a drive block (334). It will be understood that cam cylinder (332) and drive block (334) are substantially similar to cam cylinder (232) and drive block (234) of FIG. 17. Cam cylinder (332) defines a shaft opening operable to receive a drive shaft (346) as will be discussed in further detail below. Drive block (334) defines a cam opening (343) through which cam cylinder (332) extends. As seen in FIG. 24, cam opening (343) is shaped as an elongate slot. Cam opening (343) defines two diameters: D3 and D4. As seen in the illustrated version, cam cylinder (332) has roughly the same size diameter as D3, whereas cam cylinder (332) has a smaller diameter than D4. As a result of eccentricity and difference in diameters, as cam cylinder (332) rotates within cam opening (343), drive block (334) oscillates back and forth longitudinally. Drive block (334) is in communication with holder (344) which is operable to cradle shaft ring (335). Shaft ring (335) in the exemplary version is shaped to extend around only a portion of the circumference of tube (349). It will be understood that holder (344) and shaft ring (335) are substantially similar to holder (244) and shaft ring (235) of FIG. 17. Holder (344) has a half ring shape, though any suitable shape operable to cradle shaft ring (335) may be used. Shaft ring (335) is able to freely rotate while being held by holder (344). As drive block (334) translates distally and proximally, shaft ring (335) also translates distally and proximally. It will be appreciated that shaft ring (335) may be coupled with a firing beam (190) such as one seen in FIG. 8. As a result, shaft ring (335) is operable to drive firing beam (190) longitudinally along shaft assembly (302).

Housing (312) also comprises a spur gear (336), which meshes with a first rack (337) and a second rack (338). It will be appreciated that spur gear (336), first rack (237), and second rack (338) are substantially similar to spur gear (236), first rack (337) and second rack (238) of FIG. 17. First rack (337) and second rack (338) are positioned on opposing sides of spur gear (336). First rack (337) is in communication with a first half ring (341) whereas second rack (338) is in communication with a second half ring (340) through a rack arm (339). When spur gear (336) rotates, first rack (337) and second rack (338) move in opposing longitudinal directions. As a result, rotation of spur gear (336) in one direction causes first half ring (341) and second half ring (340) to spread apart whereas rotation in the opposite direction causes first half ring (341) and second half ring (340) to translate toward each other.

It will be appreciated that spur gear (336), first helical gear (330), and cam cylinder (332) are operable to engage a plurality of drive shafts (345, 346, 347). Drive shafts (345, 346, 347) are positioned such that at least two of drive shafts (345, 346, 347) are positioned on opposing sides of door (313). Drive shafts (345, 346, 347) extend upwardly, generally perpendicular to shaft assembly (302) and are aligned generally with housing (312). In particular, first drive shaft (345) is aligned with first helical gear (330) and third drive shaft (347) is aligned with spur gear (336). Second drive shaft (346) is offset from the longitudinal axis of cam cylinder (332). As a result, cam cylinder (332) is operable to rotate eccentrically in relation to drive block (334). Unlike the exemplary version shown in FIG. 14, first drive shaft (345) continually engages first helical gear (330), second drive shaft (346) continually engages cam cylinder (332), and third drive shaft (347) continually engages spur gear (336). Base (314) further comprises free shafts (373). Free shafts (373) in the exemplary version point upwardly, perpendicularly away from base (314). Free shafts (373) do not rotate and are not configured to drive any portion of interface assembly (320).

Drive shafts (345, 346, 347) are in communication with a plurality of drive plates similar to drive plates (248, 250, 251) of FIG. 19 such that the drive plates may be coupled with, for example, drive discs (120) of FIG. 10. Drive discs (120) are operable to rotate the drive plates, thereby rotating drive shafts (345, 346, 347).

Figure 15:
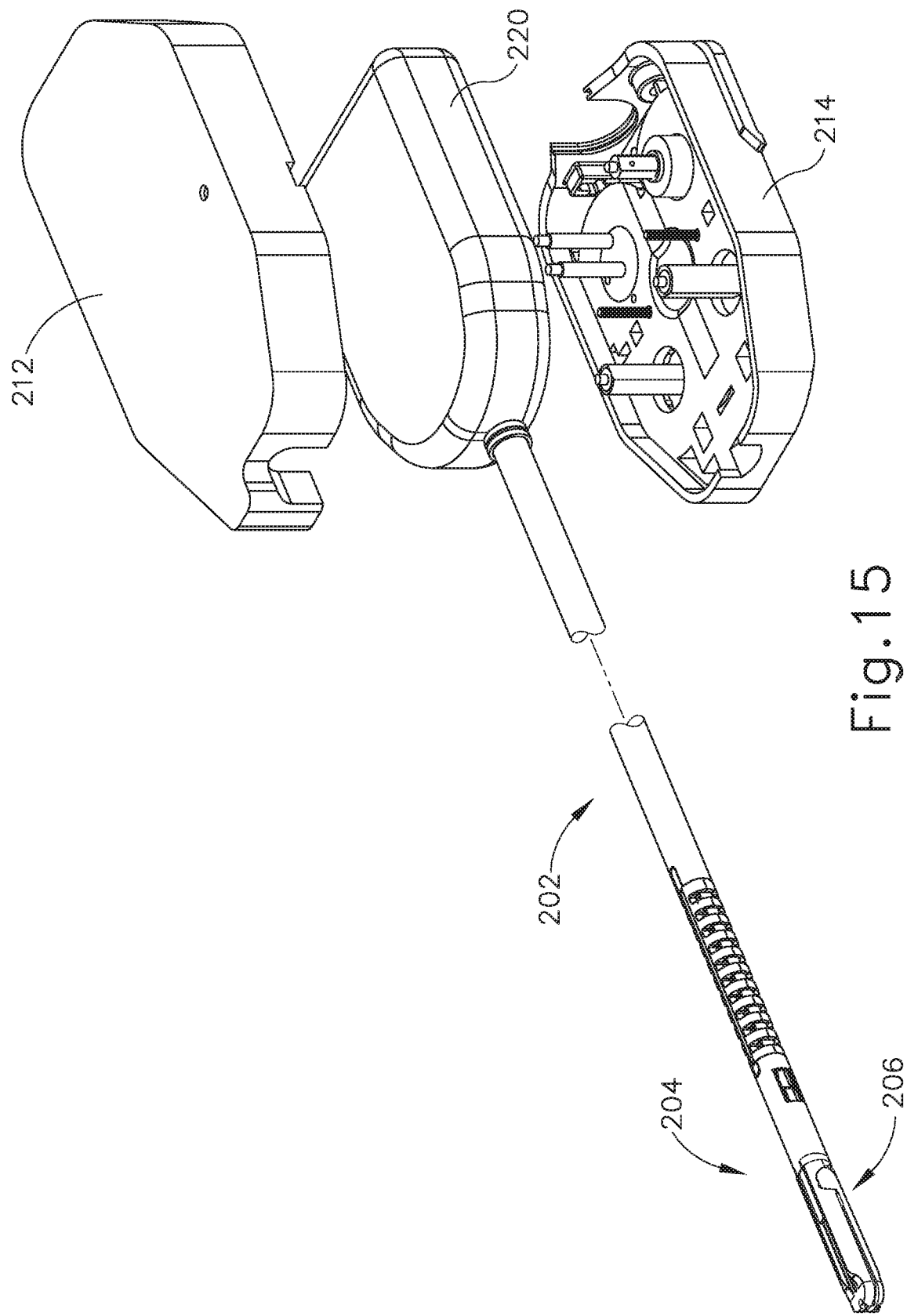
FIG. 15 depicts a top, perspective view of the surgical instrument of FIG. 14, with the housing and the base removed from the separable compartment.
Figure 16:
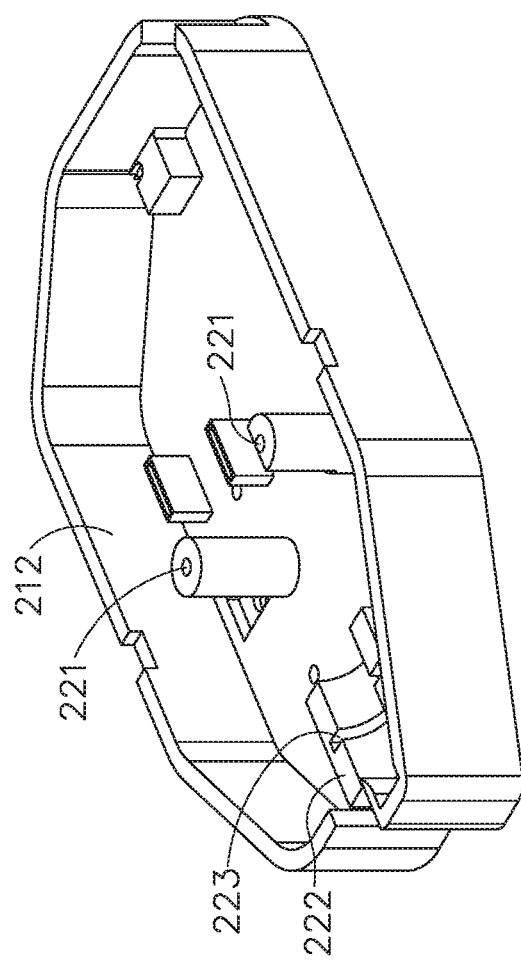
FIG. 16 depicts a bottom, perspective view of the housing of the surgical instrument of FIG. 4.

Similarly to the version shown in FIG. 15, first drive shaft (345) is operable to rotate first helical gear (330), which turns shaft helical gear (331), which rotates tube (349) of shaft assembly (302). It will be understood that first drive shaft (345) may be independently driven, and the resultant turning of shaft assembly (302) may be operable to rotate end effector (306). Rotating second drive shaft (346) is operable to actuate drive block (334) such that a firing beam may be driven longitudinally through shaft assembly (302). Finally, rotating third drive shaft (347) is operable drive first half ring (341) and second half ring (340) longitudinally toward each other or to spread them apart longitudinally. In particular, spur gear (336) causes first rack (337) and second rack (338) to move in opposing directions, thereby moving first half ring (341) and second half ring (340). It will be appreciated that the movement of first half ring (341) and second half ring (340) is operable to engage articulation beams substantially similar to articulation beams (260, 261) shown in FIG. 21 in order to communicate motion to articulation section (304) and articulate end effector (306).

Figure 25:
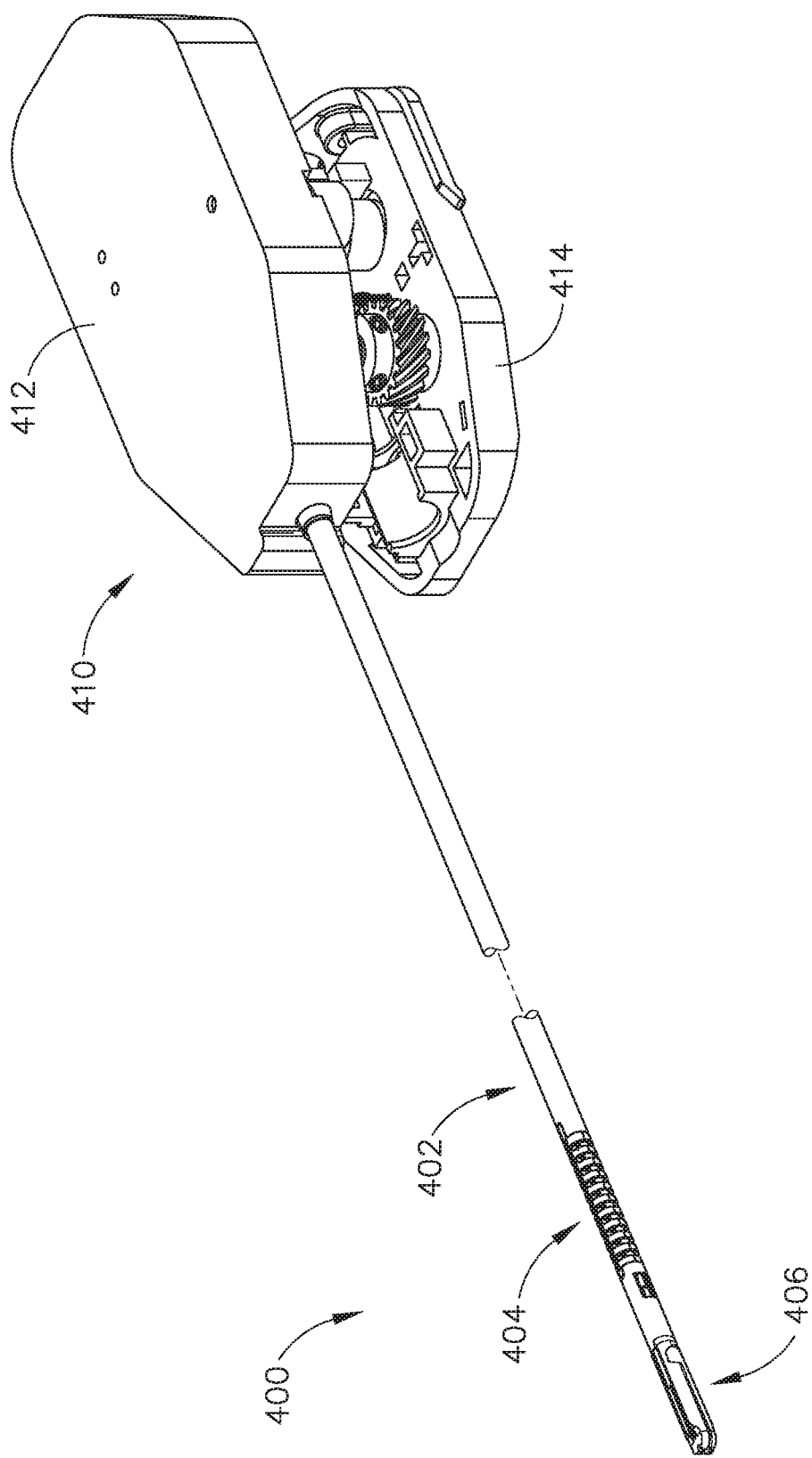
FIG. 25 depicts a top perspective view of an exemplary alternative surgical instrument for incorporation with the system of FIG. 1, with a cover separated from a base.

V. Exemplary Alternative Electrosurgical Instrument with Articulation Feature and Housing with Shaft Assembly FIG. 25 shows an exemplary alternative electrosurgical instrument (400). Instrument (400) of this example is substantially similar to instrument (100) described above in that instrument (400) has a shaft assembly (402), an articulation section (404), and an end effector (406) that are substantially identical to shaft assembly (160), articulation section (170), and end effector (180) described above. Instrument (400) of this example is also operable to couple with a dock (72) of robotic arm cart (40) via an interface assembly (410). However, interface assembly (410) of this example is different from interface assembly (110) described above.

Figure 26:
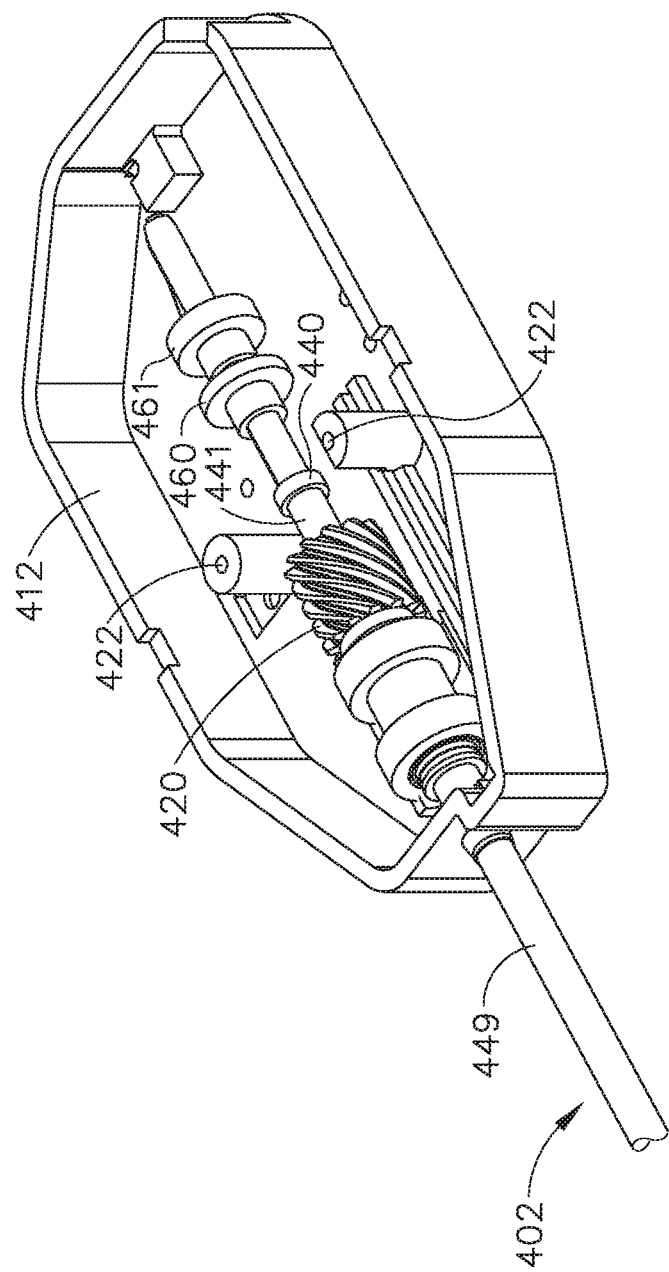
FIG. 26 depicts a bottom, perspective view of the cover of the surgical instrument of FIG. 25.

Interface assembly (410) comprises a housing (412) and a base (414). Generally speaking, interface assembly (410) differs from interface assembly (110) above in that housing (412) of interface assembly (410) incorporates shaft assembly (402). FIG. 26 shows housing (412) with shaft assembly (402) incorporated into housing (412). Specifically, shaft assembly (402) extends directly from housing (412). However, it will be appreciated that any suitable method of incorporating shaft assembly (402) and housing (412) may be used as would be apparent to one of ordinary skill in the art in view of the teachings herein. Housing (412) comprises a pair of screw holes (422) operable to receive screws (423) from base (414) such that housing (412) becomes affixed to base (414). Alternatively, housing (412) may be snap-fit to base (414), clipped to base (414), clamped to base (414), or otherwise coupled with base (414).

Shaft assembly (402) comprises a shaft helical gear (420) and a tube (449). Shaft helical gear (420) is unitarily secured to tube (449) such that shaft helical gear (420) rotates tube (449). As a result, rotating shaft helical gear (420) is operable to rotate end effector (406) with tube (449) about the longitudinal axis defined by tube (449). Furthermore, shaft assembly (402) comprises a firing ring (440) and a firing tube (441). Firing ring (440) is unitarily secured to firing tube (441) such that firing ring (440) is operable to translate firing tube (441). Firing tube (441) is slidably disposed in tube (449). Furthermore, firing tube (441) is unitarily secured to a firing beam such as firing beam (190) shown in FIG. 8. Firing ring (440) is operable to longitudinally translate, which translates firing tube (441) within tube (449) to advance the firing beam or to retract the firing beam. Shaft assembly (402) also comprises a first ring (460) and second ring (461). First and second rings (460, 461) are coupled with a pair of articulation beams such as first articulation beam (260) and second articulation beam (261) of FIG. 21 in order to communicate motion to articulation section (404) and articulate end effector (406).

Figure 27:
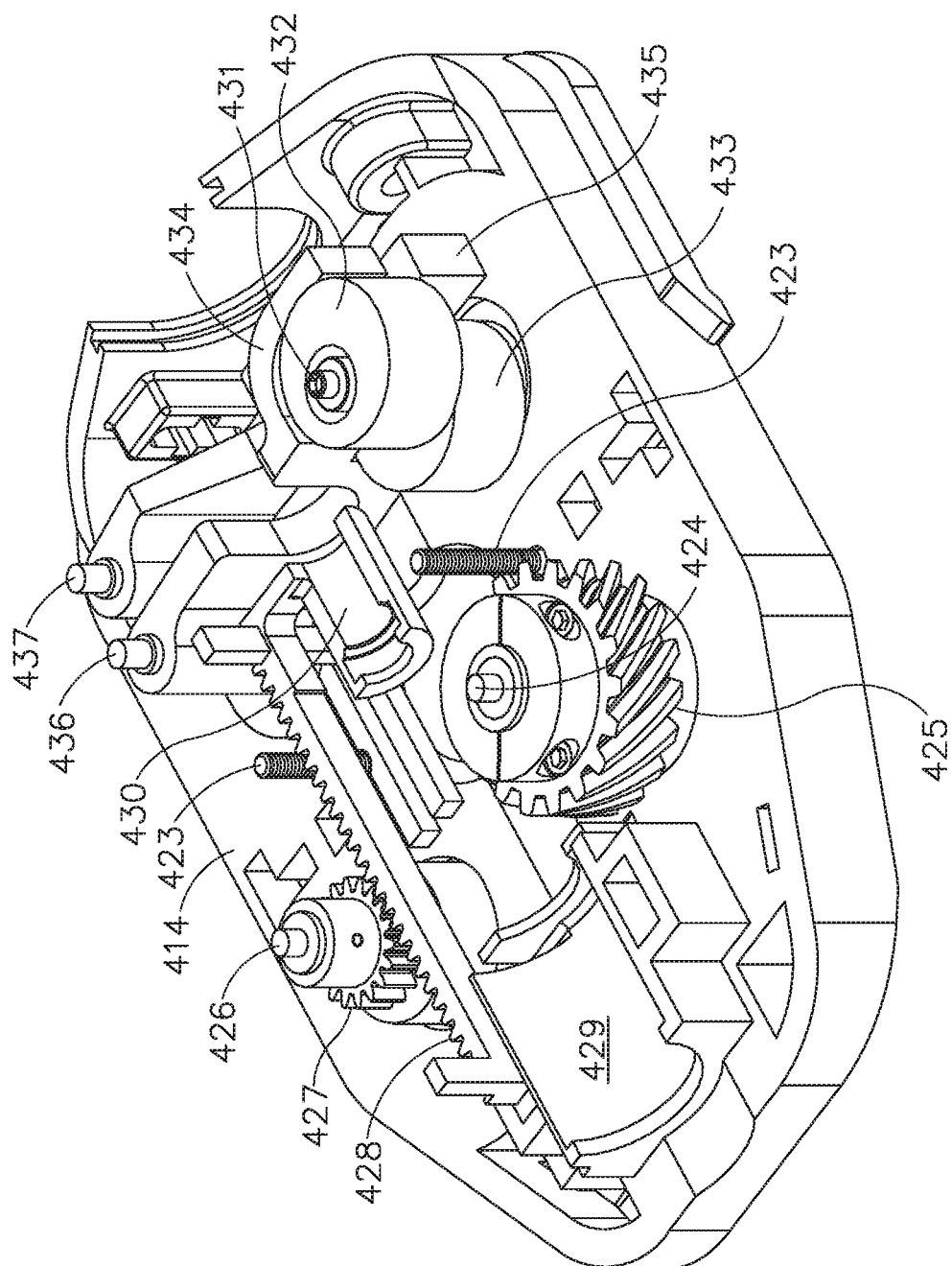
FIG. 27 depicts a top, perspective view of the base of the surgical instrument of FIG. 25.

As shown in FIG. 27, base (414) comprises a first drive shaft (424) and a first helical gear (425). First drive shaft (424) and first helical gear (425) are unitarily coupled such that rotation of first drive shaft (424) rotates first helical gear (425). Base (414) further comprises second drive shaft (426), a first spur gear (427), a rack (428), and a tube tray (430). Second drive shaft (426) and first spur gear (427) are unitarily coupled such that second drive shaft (426) rotates first spur gear (427). First spur gear (427) meshes with rack (428) such that as first spur gear (427) rotates, rack (428) advances or retracts longitudinally depending on the direction first spur gear (427) rotates. Rack (428) is coupled with tube tray (430) such that tube tray (430) advances or retracts longitudinally with rack (428). Tube tray (430) is configured to hold firing ring (440) of shaft assembly (402). As a result, second drive shaft (426) is operable to advance and retract firing ring (430), which can advance and retract a firing beam within shaft assembly (402).

Figure 28:
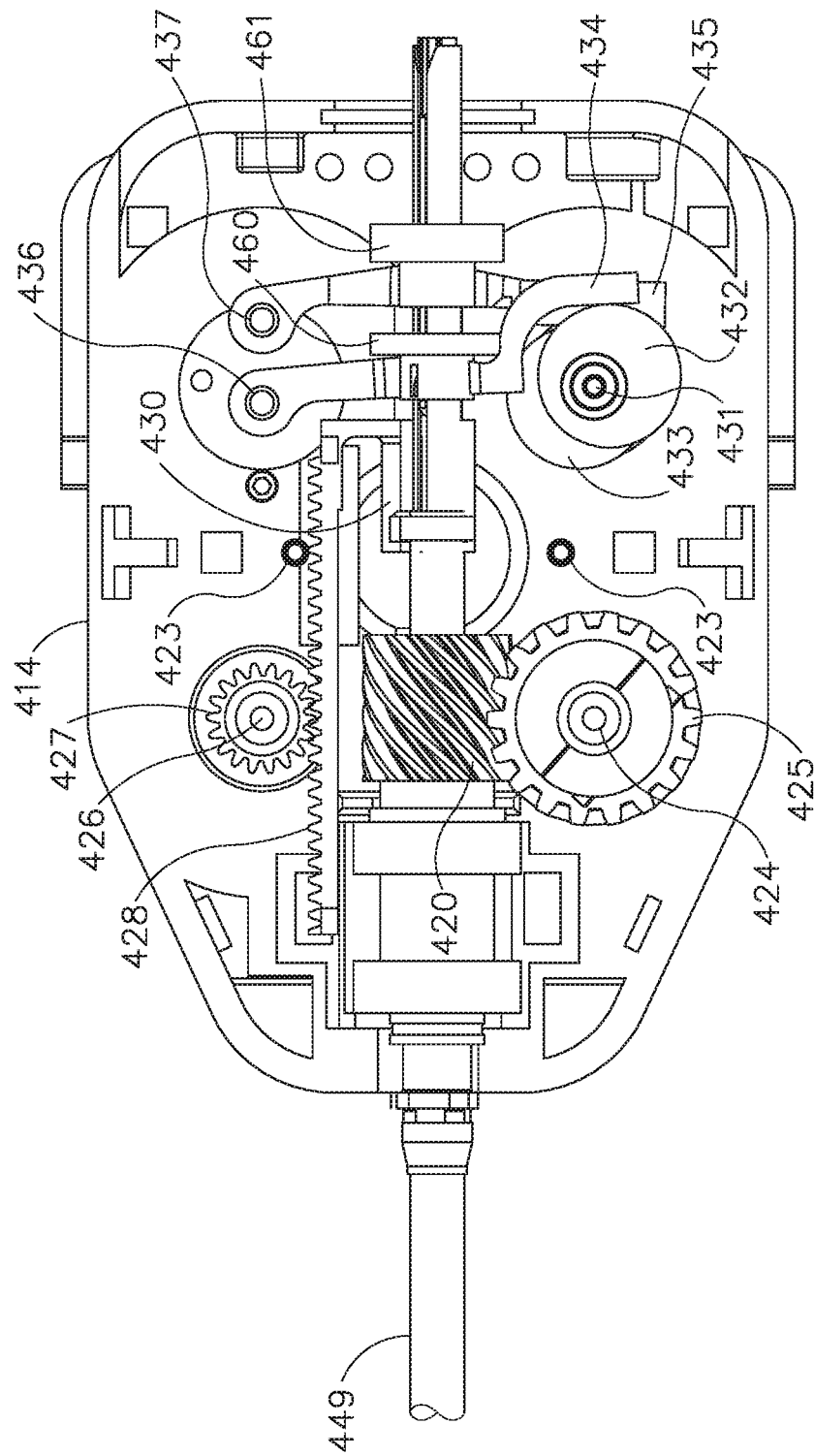
FIG. 28 depicts a top, plan, internal view of the surgical instrument of FIG. 25 with the cover housing removed.

Base (414) also comprises a third drive shaft (431), a first cam (432), a second cam (433), a first pivotal arm (434) and a second pivotal arm (435). Third drive shaft (431) is unitarily coupled with first cam (432) and second cam (433). As a result, third drive shaft (431) is operable to rotate first cam (432) and second cam (433). First cam (432) and second cam (433) are eccentrically positioned along drive shaft (431) in an opposingly offset manner such that first cam (432) and second cam (433) extend in opposing directions from third drive shaft (431). For instance, FIG. 28 shows how first cam (432) and second cam (433) are opposingly positioned in relation to third drive shaft (431).

First pivotal arm (434) and second pivotal arm (435) are operable to pivot about respective pins (436, 437). First and second pivotal arms (434, 435) are in communication with articulation beams substantially similar to articulation beams (260, 261) shown in FIG. 21 in order to communicate motion to articulation section (404) and articulate end effector (406). The following example will refer to first ring (460) as being coupled with articulation beam (260) and second ring (461) as being coupled with articulation beam (261). As drive shaft (431) rotates, first cam (432) drives first pivotal arm (434) proximally away from end effector (406). First pivotal arm (434) drives first ring (460) proximally thereby pulling articulation beam (260) proximally. This proximal movement of articulation beam causes articulation section (404) to flex toward articulation beam (260), thereby laterally deflecting end effector (406) away from the longitudinal axis of shaft assembly (402) toward articulation beam (260). This flexing of articulation section (404) pulls articulation beam (261) distally, which in turn pulls second ring (461). Due to the offset eccentric relationship of cams (432, 433), second cam (433) is positioned to allow second ring (461) to pivot second pivotal arm (435) distally when first cam (432) drives first pivotal arm (435) proximally as described above.

Drive shaft (431) may be rotated to a point where articulation section (404) reaches a maximum degree of articulation. To straighten articulation section (404) back out, the above operation may simply be reversed by reversing the rotation of drive shaft (431). Alternatively, if drive shaft (431) continues rotating in the same first direction, second cam (433) will start to pivot second pivotal arm (435) proximally, which will drive second ring (461) proximally, which will in turn pull articulation beam (261) proximally. This will pull articulation section (404) toward articulation beam (261), which will then pull articulation beam (260) distally. This distal movement of articulation beam (260) will pull first ring (460) distally, which will pivot first pivotal arm (434) distally. Again, due to the offset eccentric relationship of cams (432, 433), cam (432) will provide clearance for distal pivotal movement of first pivotal arm (434) at this stage. Drive shaft (431) may continue rotating until articulation section (404) is straightened or even until articulation section (404) begins to deflect end effector (406) laterally away from the longitudinal axis of shaft assembly (402) in a direction opposite to the articulation direction provided when first articulation beam (460) is pulled proximally. Thus, it should be understood that third drive shaft (431) is operable to articulate end effector (406) by laterally deflecting end effector (406) away from the longitudinal axis of shaft assembly (402) at articulation section (404).

Furthermore, it will be understood that first drive shaft (424), second drive shaft (426), and third drive shaft (431) are operable to engage drive discs (120) such as those shown in FIG. 10. As a result, the user may control drive discs (120) to effectuate motions described above.

VI. Miscellaneous

It should be understood that an interface assembly may include an integral power source such as a battery, and that such a battery may provide at least some of any electrical power required to operate the surgical instrument of the interface assembly. In other words, an interface assembly may provide electrical power to one or more components of the associated surgical instrument from a source that is internal to the interface assembly and/or from a source that is external to the interface assembly (e.g., through system (10)). Regardless of where the source is located, the interface assembly may include one or more conductive clips, contacts, and/or other features that provide automatic electrical coupling with the shaft assembly when the shaft assembly is mechanically coupled with the interface assembly. Various suitable ways in which a shaft assembly and an interface assembly may be electrically coupled will be apparent to those of ordinary skill in the art in view of the teachings herein.

Furthermore, an interface assembly may be configured to couple with a variety of types of modular shaft cartridges/assemblies. Such modular shaft cartridges/assemblies may provide inter-modality and/or intra-modality variation. Examples of inter-modality variation may include a single interface assembly being able to selectively couple with different shaft cartridges/assemblies having a variety of end effectors that include staplers, RF electrosurgical features, ultrasonic cutting features, etc. Examples of intra-modality variation may include a single interface assembly being able to selectively couple with different RF electrosurgical shaft cartridges/assemblies having a variety of end effectors that include straight jaws, curved jaws, etc. Other inter-modality variations and intra-modality variations will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc.

In versions where the teachings herein are applied to a surgical stapling instrument, it should be understood that the teachings herein may be combined with the teachings of one or more of the following, the disclosures of all of which are incorporated by reference herein: U.S. Pat. Nos. 7,380,696; 7,404,508; 7,455,208; 7,506,790; 7,549,564; 7,559,450; 7,654,431; 7,780,054; 7,784,662; and/or U.S. Pat. No. 7,798,386. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) an end effector operable to manipulate tissue;
    (b) a shaft assembly in communication with the end effector, wherein the shaft assembly comprises a plurality of coupling components operatively engaged with the end effector, wherein the plurality of coupling components comprises a first articulation beam and a second articulation beam; and
    (c) an interface assembly in communication with the shaft assembly, wherein the interface assembly is configured to rotate and articulate the end effector, wherein the interface assembly comprises:
        (i) a housing, wherein the shaft assembly is embedded in and extends through the housing such that the plurality of coupling components are contained within the housing; and
        (ii) a base, wherein the housing is configured to close onto the base to cooperatively define a cavity and form the interface assembly, wherein the base comprises a plurality of drive shafts configured to engage the plurality of coupling components of the shaft assembly while the housing is closed onto the base such that the plurality of coupling components and the plurality of drive shafts are all housed within the cavity, wherein the plurality of drive shafts comprise an articulation drive shaft, wherein the base comprises a first pivoting arm coupled to the first articulation beam, and a second pivoting arm coupled to the second articulation beam, wherein the articulation drive shaft is configured to rotate in a single direction to pivot the first pivoting arm and the second pivoting arm in opposing directions to thereby deflect the end effector relative to the shaft assembly.

2. The apparatus of claim 1, wherein the plurality of drive shafts of the interface assembly comprises a first drive shaft attached to a first helical gear.

3. The apparatus of claim 2, wherein the shaft assembly comprises a second helical gear.

4. The apparatus of claim 3, wherein the second helical gear is configured to operatively mesh with the first helical gear when the shaft assembly is coupled with the interface assembly.

5. The apparatus of claim 4, wherein the first drive shaft is configured to rotate the shaft assembly and the end effector about a longitudinal axis defined by a proximal portion of the shaft assembly.

6. The apparatus of claim 2, wherein the plurality of drive shafts comprises a second drive shaft attached to a cam cylinder.

7. The apparatus of claim 6, wherein the interface assembly further comprises a drive block configured to translate relative to the second drive shaft in response to rotation of the cam cylinder.

8. The apparatus of claim 7, wherein the drive block comprises a holder, wherein the shaft assembly comprises a shaft ring configured to translate relative to a proximal portion of the shaft assembly, wherein the holder is configured to house the shaft ring when the shaft assembly is coupled with the interface assembly.

9. The apparatus of claim 8, wherein the shaft assembly further comprises a firing beam, wherein the shaft ring is coupled to the firing beam.

10. The apparatus of claim 9, wherein the firing beam extends into the end effector.

11. The apparatus of claim 1, wherein the shaft assembly extends along a longitudinal axis.

12. The apparatus of claim 11, wherein the plurality of drive shafts comprises a first drive shaft, wherein the first drive shaft is configured to rotate the shaft assembly about the longitudinal axis.

13. An apparatus comprising:
(a) an end effector operable to manipulate tissue;
(b) a shaft assembly in communication with the end effector, wherein the shaft assembly comprises a plurality of coupling components configured to control the end effector; and
(c) an interface assembly in communication with the shaft assembly, wherein the interface assembly is configured to rotate and articulate the end effector, wherein the interface assembly comprises:
(i) a housing comprising a pair of screw receiving bodies, wherein the plurality of coupling components comprises a first articulation beam and a second articulation beam; and
(ii) a base, wherein the housing is configured to close onto the base to form the interface assembly, wherein the base comprises a plurality of drive shafts configured to engage the plurality of coupling components of the shaft assembly while the housing is closed onto the base, wherein the plurality of drive shafts are oriented perpendicularly in relation to the shaft assembly, wherein the base comprises a first eccentric cam and a second eccentric cam in communication with the first articulation beam and the second articulation beam, respectively, wherein the first eccentric cam and the second eccentric cam are configured to unitarily rotate to thereby drive the first articulation beam and the second articulation beam in opposing directions.

14. An apparatus comprising:
(a) an end effector operable to manipulate tissue;
(b) a shaft assembly in communication with the end effector, wherein the shaft assembly comprises a plurality of coupling components operatively engaged with the end effector, where the plurality of coupling components comprises a pair of articulation beams; and
(c) an interface assembly in communication with the shaft assembly, wherein the interface assembly is configured to rotate and articulate the end effector, wherein the interface assembly comprises:
(i) a housing, wherein the shaft assembly is embedded in and extends through the housing such that the plurality of coupling components are contained within the housing; and
(ii) a base comprising a plurality of drive shafts oriented perpendicularly in relation to the shaft assembly, wherein the housing is configured to close onto the base in a direction parallel to the orientation of the plurality of drive shaft in order to cooperatively define a cavity and form the interface assembly, wherein the base comprises a plurality of drive shafts configured to engage the plurality of coupling components of the shaft assembly while the housing is closed onto the base, wherein the base comprises a pair of eccentric cams configured to unitarily rotate, wherein the base further comprises a pair of pivot arms coupled with a respective articulation beam of the pair of articulation beams, wherein the pair of pivot arms are associated with the pair of eccentric cams and are configured to drive the pair of articulation beams in opposite directions in response to the pair of eccentric cams rotating in a single direction.

15. The apparatus of claim 14, wherein the end effector comprises a pair of jaws.

16. The apparatus of claim 15, wherein the end effector comprises a first electrode associated with a first jaw of the pair of jaws.

17. The apparatus of claim 16, wherein the end effector further comprise a second electrode associated with a second jaw of the pair of jaws.

18. The apparatus of claim 14, wherein the pair of eccentric cams comprise a pair of eccentric cam cylinders.

* * * * *